United States Patent [19]
Haynes et al.

[11] Patent Number: 5,723,437
[45] Date of Patent: Mar. 3, 1998

[54] CD6 LIGAND

[75] Inventors: Barton F. Haynes, Durham, N.C.; Alejandro Aruffo, Edmonds, Wash.; Dhavalkumar Patel, Durham, N.C.

[73] Assignees: Duke University, Durham, N.C.; Bristol-Myers Squibb Company, New York, N.Y.

[21] Appl. No.: 333,350

[22] Filed: Nov. 2, 1994

Related U.S. Application Data

[63] Continuation-in-part of Ser. No. 143,903, Nov. 2, 1993, abandoned.

[51] Int. Cl.$^6$ .................. A61K 38/17; C07K 14/435
[52] U.S. Cl. ................. 514/2; 530/350; 530/413; 435/69.1
[58] Field of Search ................. 530/350, 413; 435/69.1; 514/2

[56] References Cited

PUBLICATIONS

Wee et al, "Characterization of a CD6 Ligand(s) Expressed on Human–and Murine–Derived Cell Lines and Murine Lymphoid Tissues", Cellular Immunology 158:353–364 (1994).

Aruffo et al, "The Lymphocyte Glycoprotein CD6 Contains a Repeated Domain Structure Characteristic of a New Family of Cell Surface and Secreted Proteins", J. Exp. Med. 174:949–952 (1991).

Kamoun et al, "A Novel Human T Cell Antigen Preferentially Expressed on Mature T Cells and Shared By Both Well and Poorly Differenitated B Cell Leukemias and Lymphomas", The Journal of Immunology 127(3):987–991 (1981).

Gangemi et al, "Anti–T12, An Anti–CD6 Monoclonal Antibody, Can Activate Human T Lymphocytes", The Journal of Immunology 143:2439–2447 (1989).

Morimoto et al, "2H1—A Novel Antigen Involved in T Lymphocyte Triggering", The Journal of Immunology, 140:2165–2170 (1988).

Wee et al, "Tyrosine Phosphorylation of CD6 by Stimulation of CD3: Augmentation by the CD4 and CD2 Coreceptors", J. Exp. Med. 177:219–223 (1993).

Soiffer et al, "Prevention of Graft–Versus–Host Disease by Selective Depletion of CD6–Positive T Lymphocytes from Donor Bone Marrow", Journal of Clinical Oncology 10(7):1191–1200 (1992).

Vollger et al, "Thymocyte Binding to Human Thymic Epithelial Cells is Inhibited by Monoclonal Antibodies to CD–2 and LFA–3 Antigens", The Journal of Immunology 138:358–363 (1987).

Swack et al, "Biosynthesis and Post–translational Modification of CD6, a T Cell Signal–transducing Molecule", The Journal of Biological Chemistry 266(11):7137–7143 (1991).

Pawelec and Buhring, "Monoclonal Antibodies to CD6 Preferentially Stimulate T–Cell Clones with γ/δ Rather Than α/β Antigen Receptors", Human Immunology 31:165–169 (1991).

Mayer et al, "Expression of the CD6 T lymphocyte differentiation antigen in normal human brain", Journal of Neuroimmunology 29:193–202 (1990).

Aruffo et al, "Granule membrane protein 140 (GMP140) binds to carcinomas and carcinoma–derived cell lines", Proc. Natl. Acad. Sci. USA 89:2292–2296 (1992).

Pesandro et al, "Antibody–Induced Antigenic Modulation is Antigen Dependent: Characterization of 22 Proteins on a Malignant Human B Cell", The Journal of Immunology 137(11):3689–3695 (1986).

Patel et al, "Human Thymic Epithelial Cells Express A Ligand for CD6 Which Mediates Binding to Mature Thymocytes", Clinical Res. 41(2):220A (1993).

Swack et al, "Structural Characterization of CD6: Properties of Two Distinct Epitopes Involved in T Cell Activation", Molecular Immunology 26(11):1037–1049 (1989).

Sims et al, "cDNA Expression Cloning of the IL–1 Receptor, a Member of the Immunoglobulin Superfamily", Science 241:585–589 (1988).

*Primary Examiner*—Stephen Walsh
*Assistant Examiner*—Sally P. Teng
*Attorney, Agent, or Firm*—Nixon & Vanderhye P.C.

[57] ABSTRACT

The present invention relates, in general, to CD6 and, in particular, to a CD6 ligand present on the surface of thymic epithelial cells, monocytes, activated T cells and a variety of other cells types. The invention further relates to methods of inhibiting the interaction of CD6 and the CD6 ligand, and to the methods of screening componunds for their ability to inhibit that interaction.

6 Claims, 23 Drawing Sheets

CHARACTERIZATION OF THE CD6 LIGAND(S)

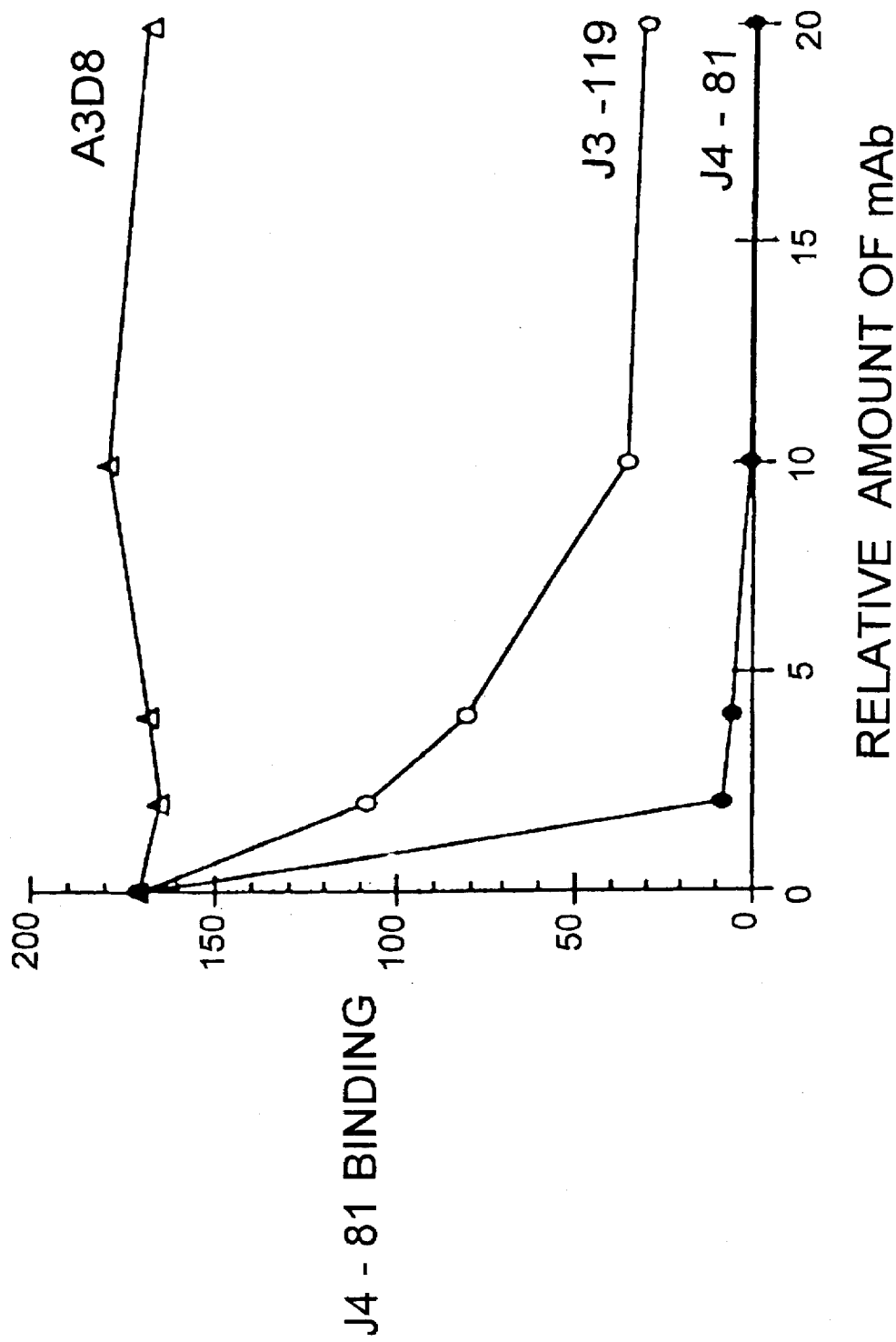

CD6 LIGAND

This is a continuation-in-part of application Ser. No. 08/143,903, filed Nov. 2, 1993, now abandoned, the entirety of which is incorporated herein by reference.

This invention was made with Government support under Grant Nos. CA-28936 and AI-07217 awarded by the National Institutes of Health. The Government has certain rights in this invention.

FIELD OF THE INVENTION

The present invention relates, in general, to CD6 and, in particular, to a CD6 ligand present on the surface of thymic epithelial cells, monocytes, activated T cells and a variety of other cell types. The invention further relates to methods of inhibiting the interaction of CD6 and the CD6 ligand, and to methods of screening compounds for their ability to inhibit that interaction.

BACKGROUND

CD6 is a 130 kDa glycoprotein that is homologous to CD5 and the macrophage scavenger receptor (Aruffo et al, J. Exp. Med. 174:949 (1991)). CD6 is expressed on the surface of mature thymocytes, peripheral T cells and a subset of B cells (Kamoun et al, J. Immunol. 127:987 (1981)). CD6 appears to be involved in T cell activation since monoclonal antibodies (mabs) to CD6 augment T cell receptor (TCR) mediated activation of T cells (Gangemi et al, J. Immunol. 143:2439 (1989)), and the CD6 molecule is tyrosine phosphorylated during TCR-mediated T cell triggering (Wee et al, J. Exp. Med. 177:219 (1993)). Mabs to CD6 have been shown to be clinically useful for the deletion of T cells for allogeneic bone marrow transplantation (Soiffer et al, J. Clin. Oncol. 10:1191 (1992)).

Results obtained by screening a panel of mabs to T cell surface antigens for their ability to inhibit the binding of thymocytes to human thymic epithelial cells (TEC) suggested that CD6 is involved in the binding of thymocytes to TEC (Vollger et al, J. Immunol. 138:358 (1987)). The present invention relates to a ligand for CD6 involved in that binding.

OBJECTS AND SUMMARY OF THE INVENTION

It is the general object of the invention to provide a CD6 ligand.

It is a specific object of the invention to provide a CD6 ligand in isolated form.

It is a further object of the invention to provide a method of inhibiting the binding of CD6 to a CD6 ligand.

It is yet another object of the invention to provide a method of screening compounds for their ability to inhibit CD6 /CD6 ligand binding.

In one embodiment, the present invention relates to an isolated CD6 ligand, including both divalent cation dependent and divalent cation independent forms thereof. The invention further relates to mimetopes of such a ligand.

In a further embodiment, the present invention relates to a method of inhibiting binding of CD6 present on the surface of a first cell to CD6 ligand present on the surface of a second cell. The method comprises contacting the CD6 present on the surface of the first cell with a soluble CD6 ligand, or mimetope thereof, under conditions such that the soluble CD6 ligand, or mimetope thereof, binds to the CD6 present on the surface of the first cell and thereby inhibits binding of the CD6 ligand present on the surface of the second cell to the CD6 present on the surface of the first cell. Alternatively, the method comprises contacting the CD6 ligand present on the surface of the second cell with soluble CD6, or mimetope thereof, under conditions such that the soluble CD6, or mimetope thereof, binds to the CD6 ligand present on the surface of the second cell and thereby inhibits binding of the CD6 present on the surface of the first cell to the CD6 ligand present on the surface of the second cell.

In another embodiment, the present invention relates to a method of screening a test compound for the ability to inhibit binding of CD6 to CD6 ligand. The method comprises: i) contacting the test compound with one of CD6 and CD6 ligand under conditions such that a complex between CD6 ligand and the CD6 or CD6 ligand can form, ii) contacting the combination of CD6 or CD6 ligand and test compound resulting from step (i) with the other of CD6 and CD6 ligand under conditions such that complexation between the CD6 and the CD6 ligand can occur, and iii) determining the extent of complexation between the CD6 and the CD6 ligand and thereby the ability of the test compound to inhibit binding of the CD6 to the CD6 ligand.

Further objects and advantages of the present invention will be clear from the description that follows.

9, A063, A065, A070, A074, A080, A090, A092, A107, A110, A113, A124, A132, A139, A141, A145, B002, B003, B005-6, B011-2, B014, B019, B025, B027-9, B031, B046, B049, B052, B055-7, B059, B068, CB10, CB22, CB27, E001, E015, E031, E045, E050, E053-4, E056-7, M01-2, M09, M14-5, M25, M32, M35-8, M43-4, MR1, MR4, MR6, MR9, MR12, MR14, XB001, NK32, P005, P012, P023, P036, P044, P098, P107-8, S009, S013, S023-4, S031, S075, S107, S188, S201, S241, S245, S252, S263, S271, S273-4, 5T-015, 5T-076, 5T-080, 5T-084, CD24.3, CD40.2, CD73.1, CD74.1 and CD77.1. Anti-integrin mabs used were: TS2/7, P1H6, 12F1, P1B5, P4G9, B5610, P3010, EA-1-6, 135-13C, P502, P309, K20, B4, P3G8, P3G2, P1H12 and TS2/16. The cells were pre-incubated with mabs at a dilution of 1:100 for 15 min at 4° C. followed by incubation with 5 μg of either CD5-Ig or CD6-Ig. Cells were washed and fusion proteins detected by reaction with fluorescein conjugated antiserum specific to the Fc portion of human IgG and flow cytometry. Specific binding was determined to be the difference in fluorescence of CD6-Ig binding and CD5-Ig binding. The binding compared to control mab (P3) is shown. There were four instances where goat anti-human IgG-Fc cross reacted with the test mab (A024, B049, 5T-084 and CD73.1). Mab J4-81 (S252) inhibited CD6-Ig binding by 56±5% (N=2).

Figure 5:
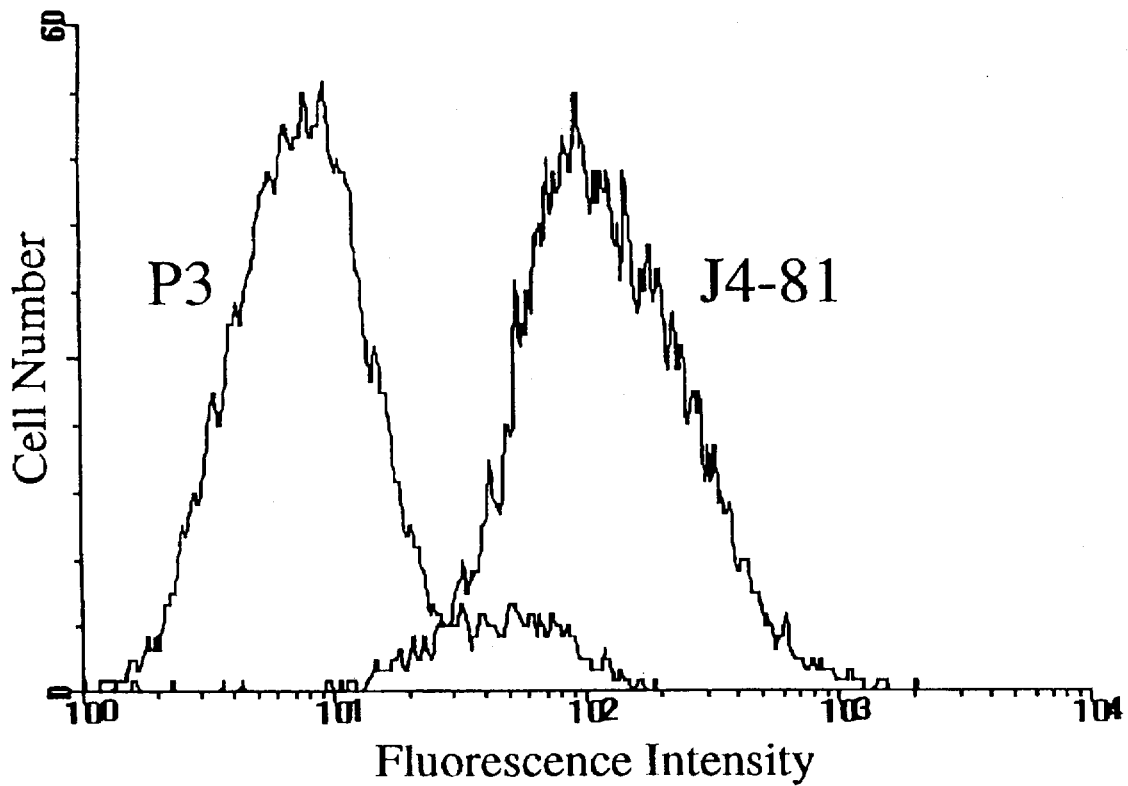

FIG. 5. Mab J4-81 reacts strongly with the surface of all cultured TEC. Cultured TEC were incubated with mab J4-81 (S252 from the Vth International Workshop on Human Leukocyte Differentiation Antigens) and control mab (P3) for 30 min at 4° C. Following a wash with PBS containing 2% BSA, bound antibodies were detected by reaction with fluorescein conjugated goat anti-mouse IgG followed by flow cytometry. Shown are the fluorescence profiles of control mab (P3) and the mab against a CD6 ligand (J4-81).

Figure 6A:
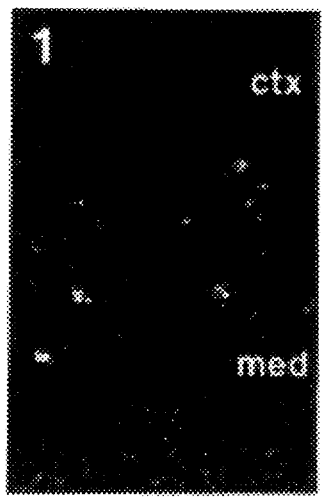
Figure 6B:
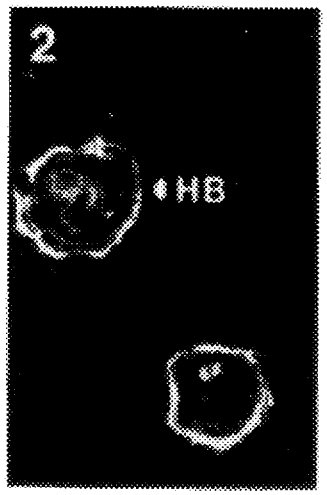

FIG. 6. Expression of CD6 and its ligand in postnatal human thymus. CD6 and its ligand in frozen human thymus sections (4 μm) were labelled by indirect immunofluorescence using mabs T12 and S252 (J4-81), respectively. Panel 1 shows the pattern of reactivity to T12 and panel 2 shows the pattern of reactivity to mab J4-81. At least three different thymus tissues were analyzed with similar results. CD6 was expressed on thymocytes in the medulla (med) and moderately on thymocytes in the cortex (ctx). Mab J4-81 detected medullary thymic epithelial cells and Hassal's bodies (HB).

Figure 7:
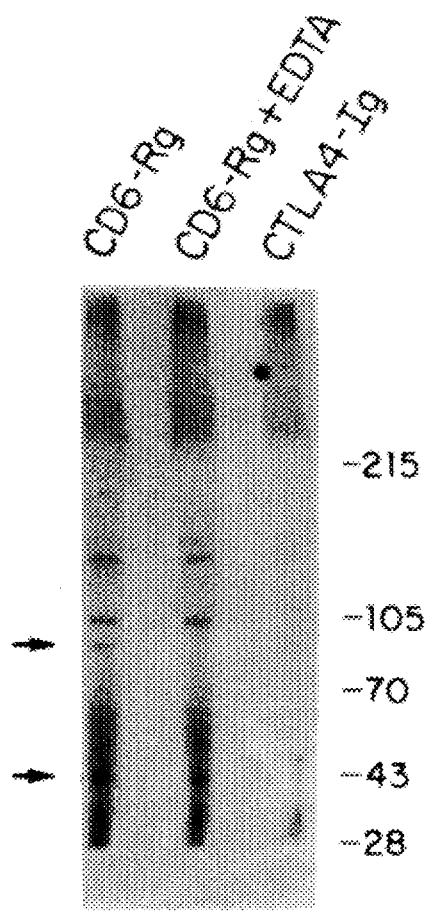

FIG. 7. Immunoprecipitation of radioactively labelled glycoproteins from metabolically labelled TEC with CD6-Ig. Cells were labelled with 6-$^3$H-glucosamine for 48 hours, lysed and lysates were immunoprecipated with CD6-Ig and with CTLA4-Ig as a control. CD6-Ig immunoprecipitation of TEC lysates was carried out with and without inclusion of 15 mM EDTA. The immunoprecipitation of a 105 kDa molecule and a 35 kDa molecule by CD6-Ig was divalent cation independent and the immunoprecipitation of an additional 90 kDa molecule by CD6-Ig was divalent cation dependent.

Figure 8:
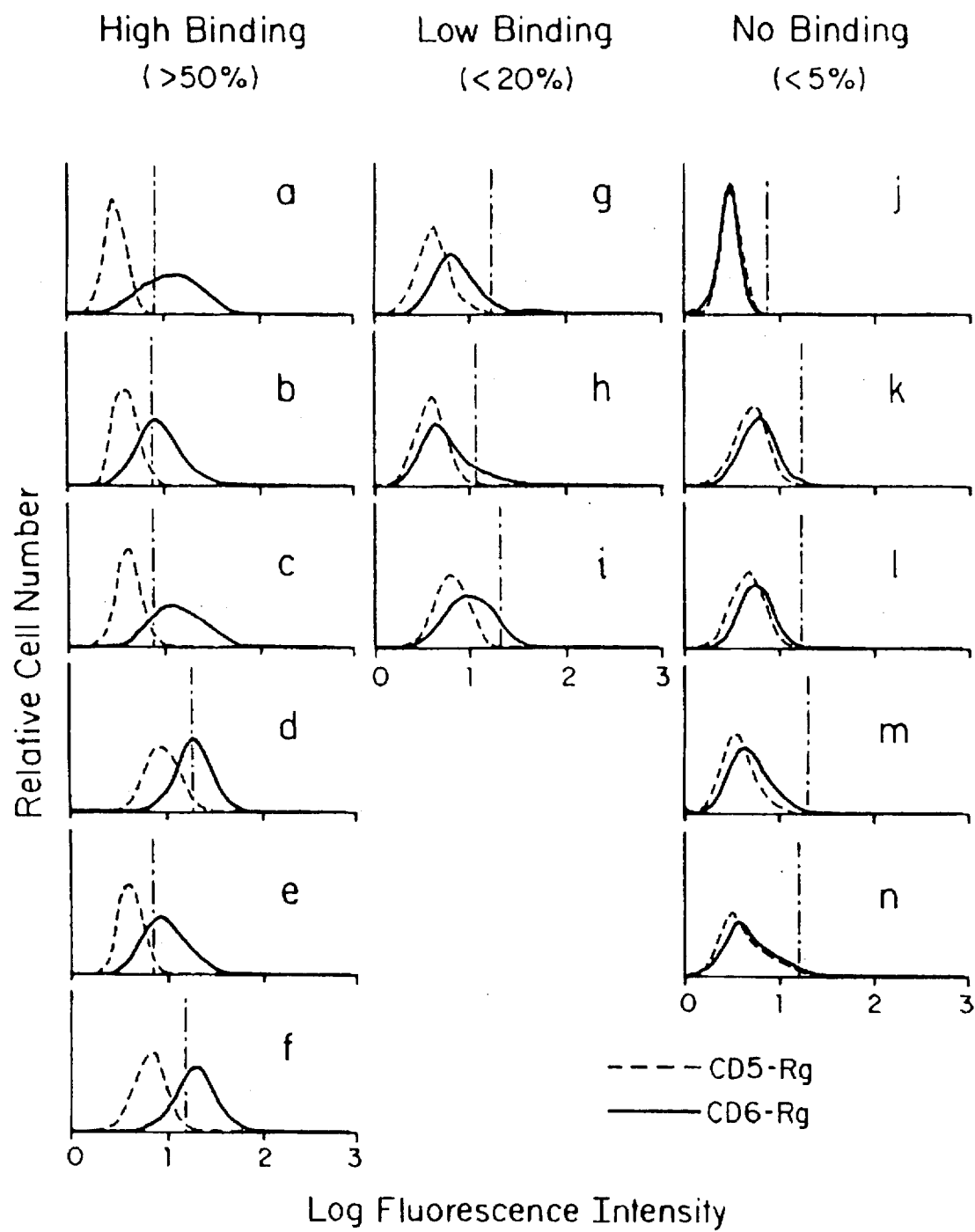

FIG. 8. CD6-Rg (=CD6-Ig) binds to a number of human-derived cell lines. Binding of CD6-Rg (solid line) and CD5-Rg (dashed line) to a number of human cell lines was examined by flow cytometry. The cell lines were grouped into three categories based on their ability to bind CD6-Rg high binding, low binding, and no binding. The percentage binding used to group cells into these three categories is based on the number of cells whose fluorescence intensity is greater than that of cells stained with the isotype matched CD5-Rg fusion protein (vertical dash-dot line). The human cell lines examined were: (a) HBL-100, (b) H3719, (c) H3606, (d) LCL8664, (e) GM0833, (f) IMR90, (g) Jurkat, (h) Peer, incubated (i) HUT78, (j) HPB-ALL, (k) JM, (l) H9, (m) LTR228, and (n) Raji. A total of $10^4$ cells were analyzed in each experiment.

Figure 9A:
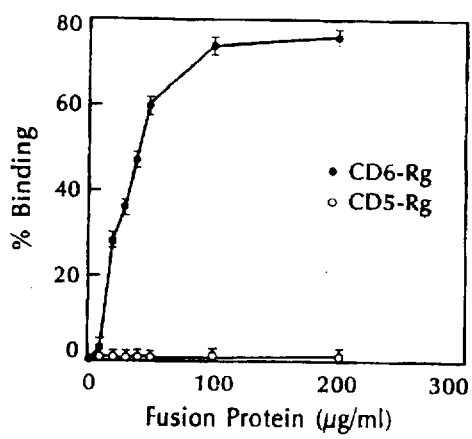

FIG. 9. CD6-Rg binding is saturable and trypsin sensitive. (A) The binding of increasing concentrations of CD6-Rg and CD5-Rg to the breast carcinoma cell line HBL-100 was examined by flow cytometry. The percentage binding (ordinate) was determined as described in FIG. 8. A total of $10^4$ cells were examined at each protein concentration. (B) The binding of CD6-Rg to HBL-100 cells which were pretreated with trypsin was compared to the binding of CD6-Rg and CD5-Rg to untreated HBL-100 cells by flow cytometry. This figure shows the results of a representative experiment out of three. Trypsin digests were carried out as described.

Figure 10:
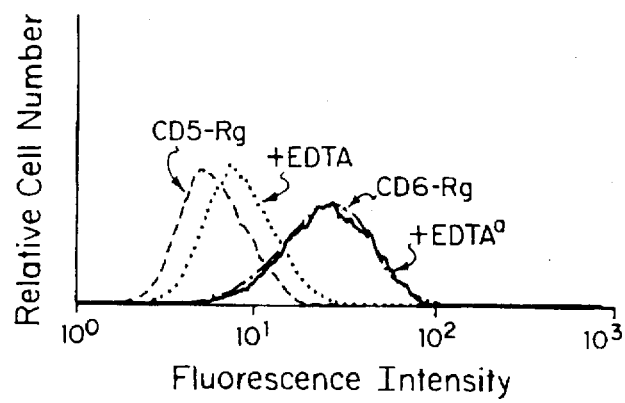

FIG. 10. CD6-Rg binding is divalent cation dependent. The binding of CD6-Rg to HBL-100 cells in the presence of EDTA (+EDTA, dotted line) was compared to the binding of CD6-Rg (dash-dot line) and CD5-Rg (dashed line) by flow cytometry. The effect of EDTA on CD6-Rg binding to HBL-100 cells was also examined after the CD6-Rg/HBL-100 complexes were allowed to form (+EDTA, solid line). A total of $10^4$ cells were examined in each experiment.

Figure 11:
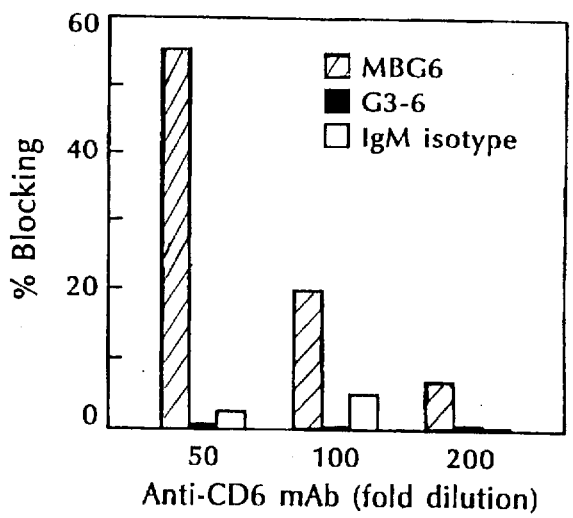

FIG. 11. CD6-Rg binding is blocked by an anti-CD6 mAb. The ability of two different anti-CD6 mAb (MBG6 and G3-6) and an irrelevant IgM mAb to block the binding of CD6-Rg to HBL-100 cells was examined by flow cytometry. In each case serial dilution of the antibodies was tested.

Figure 12A:
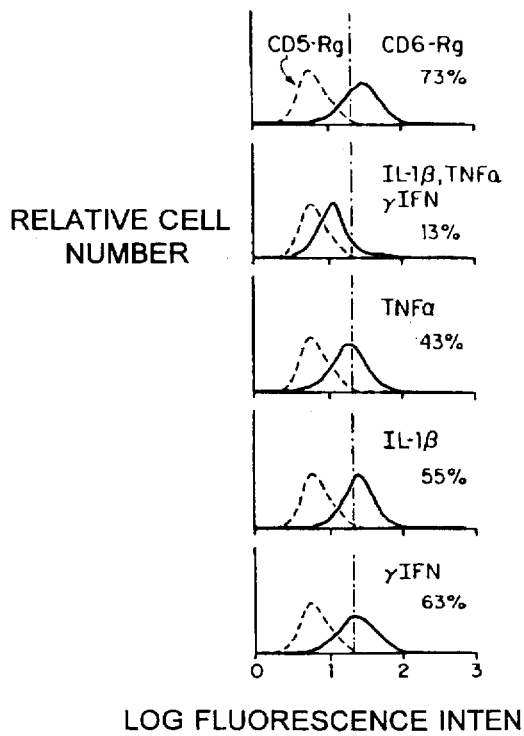
Figure 12B:
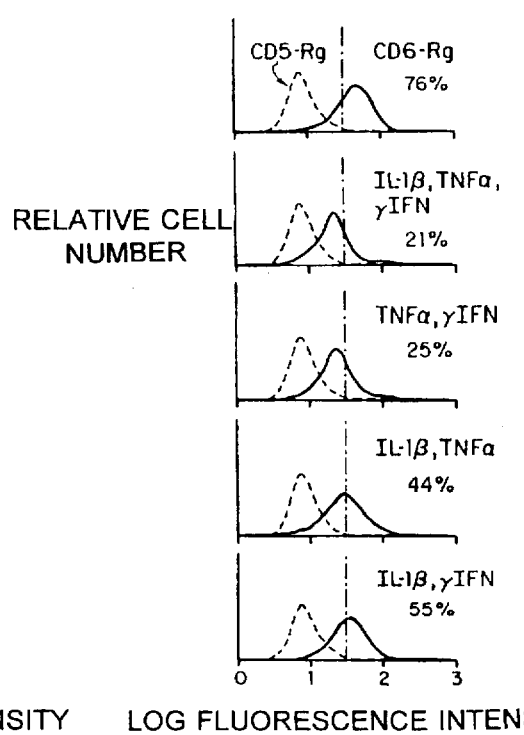

FIG. 12. CD6-Rg binding is modulated by cytokines. The biding of CD6-Rg (solid line) and CD5-Rg (dashed line) to untreated HBL-100 cells or HBL-100 cells treated with the indicated cytokines was examined by flow cytometry. The percentage of HBL-100 cells whose fluorescence intensity is to the right of an arbitrary marker (dash-dot line) following CD6-Rg binding is noted in each panel. The data shown in columns (A) and (B) represent two different experiments.

Figure 13:
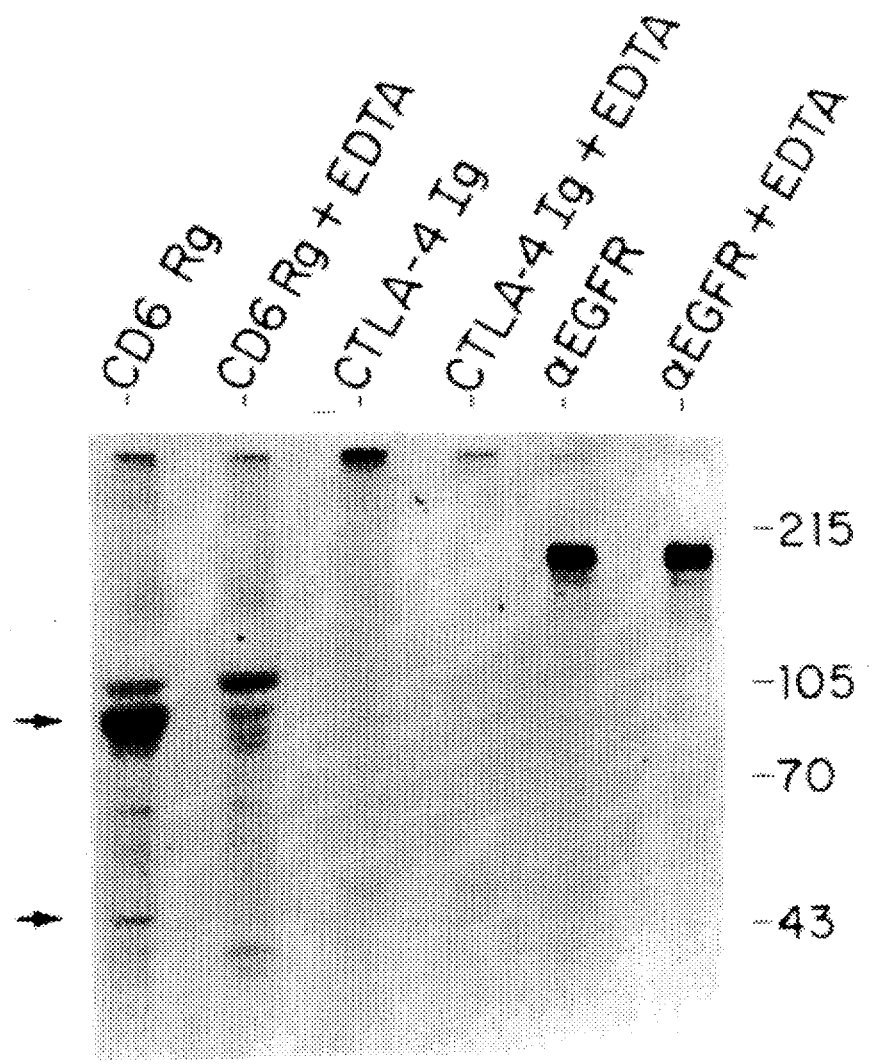

FIG. 13. Immunoprecipitation of CD6-Rg binding protein (s). HBL-100 cells were radiolabeled with [$^3$H]glucosamine. Protein(s) reactive with either CD6-Rg CTLA4-Ig, or an anti-EGF receptor mAb were immunoprecipitated from cell lysates in the absence or presence of EDTA and analyzed by SDS-PAGE. The arrows point to the two radiolabeled polypeptides which bound to CD6-Rg in the absence of EDTA. Molecular masses are given in kDa.

FIG. 14. CD6-Rg binds to cells in lymphoid organs. (A) CD6-Rg binding to skin. Scattered cells in the dermis are labeled. Nonspecific labeling of hair shafts is indicated by arrows. (B) Reactivity of human IgG1 with a serial skin section. Only weak labeling of hair shafts is evident (arrows). (C) Reactivity of CD6-Rg with thymus tissue. A delicate reticular labeling pattern is present in the cortex. (D) Reactivity of human IgG1 with thymus tissue. Only faint background labeling was detected. (E) Reactivity of CD6-Rg with lymph node. Cells in the intermediate or paracortical sinuses were labeled. (F) No binding of human IgG1 to lymph node tissue was observed.

Figure 15:
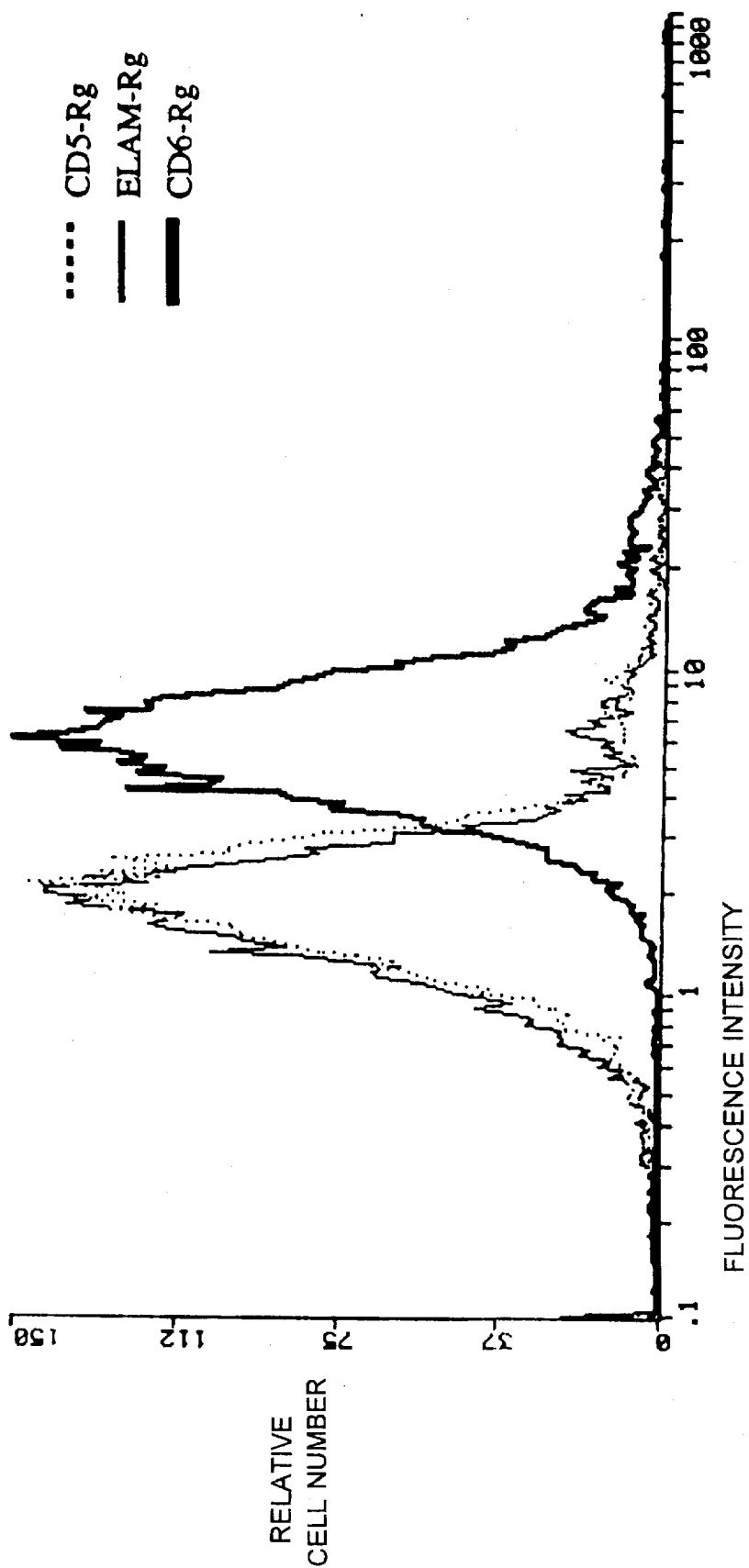

FIG. 15. Human epidermal keratinocytes express a surface ligand(s) for CD6. Shown are the reactivities of cultured epidermal keratinocytes with CD6-Rg, CD5-Rg, or ELAM1-Rg. Cells were incubated with 5 μg of fusion protein in PBS containing 2% BSA and washed. The fusion proteins were labeled with fluorescein conjugated goat anti-serum to human IgG and assayed by flow cytometry.

Figure 16A:
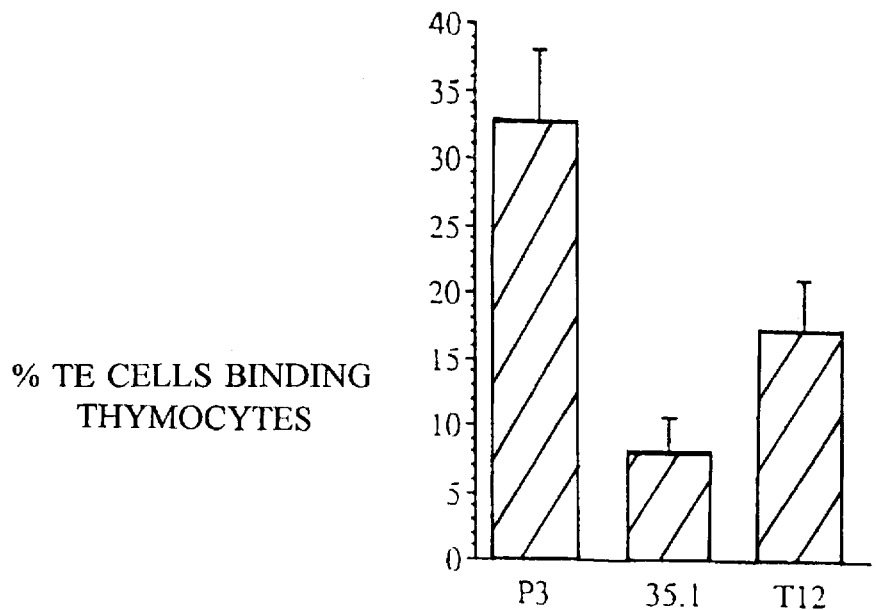
Figure 16B:
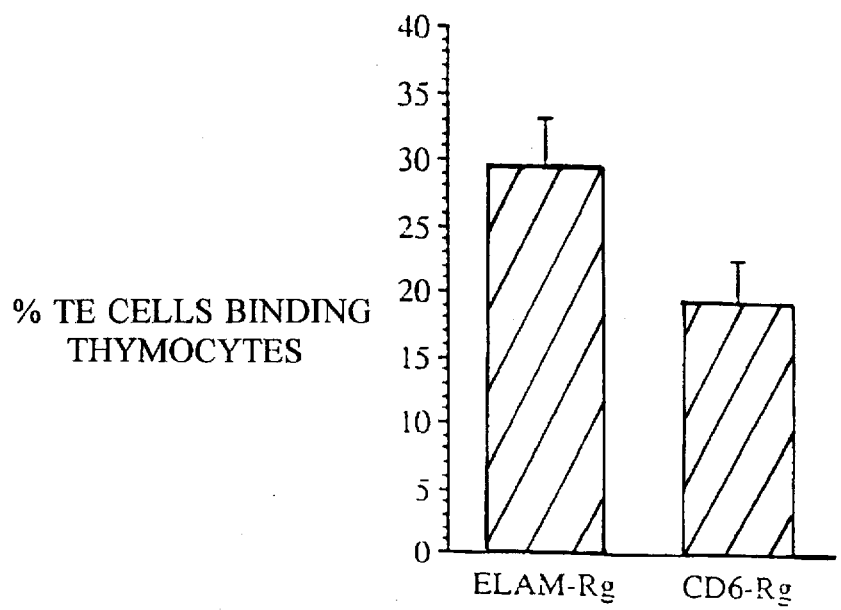

FIG. 16. CD6-CD6 ligand interactions mediate TE-thymocyte binding. Shown is a summary of 5 separate TE-thymocyte binding experiments. Panel A depicts the amount of rosette formation in the presence of specific antibodies and panel B depicts the amount of rosette formation in the presence of fusion proteins. Standard errors are indicated by bars. Both anti-CD6 antibody and CD6-Rg fusion protein partially inhibit TE-thymocyte binding: T12 inhibited rosette formation by 49±9% and CD6-Rg inhibited rosette formation by 35±9%. The differences in binding between control and 35.1 ($p<0.003$), T12 ($p<0.015$) and CD6-Rg ($p<0.05$) were statistically significant.

Figure 17A:
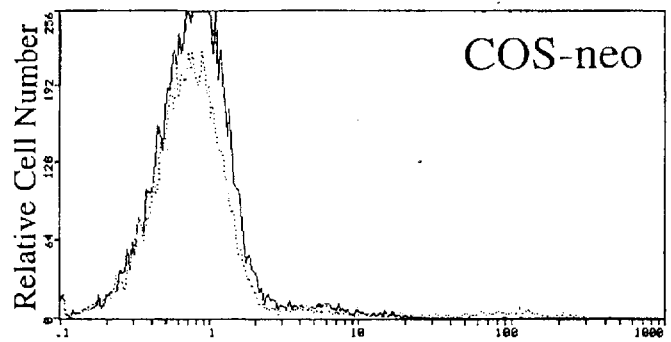
Figure 17B:
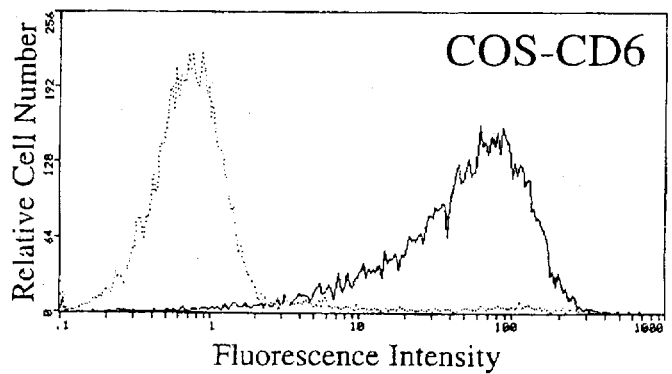
Figure 17C:
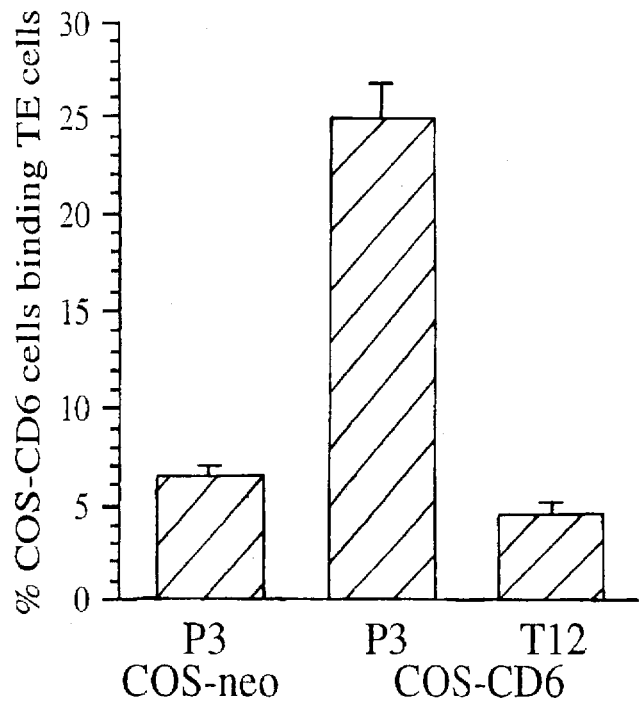
Figure 18A:
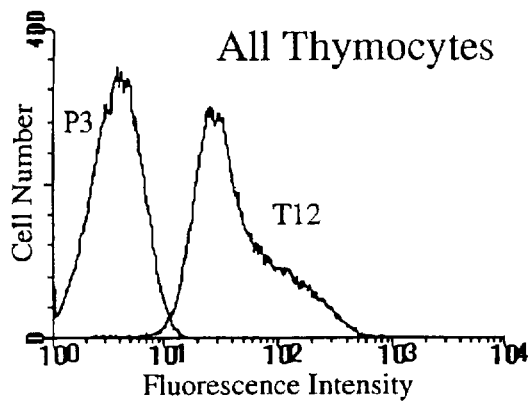
Figure 18B:
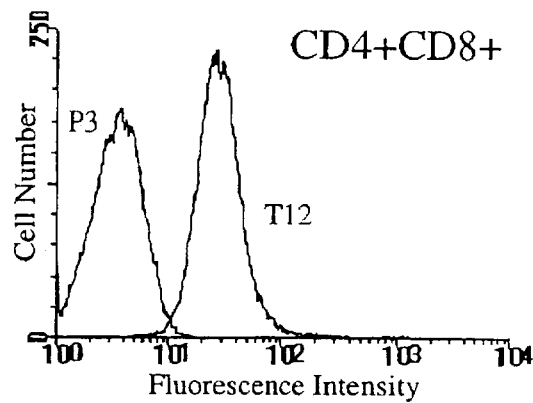
Figure 18C:
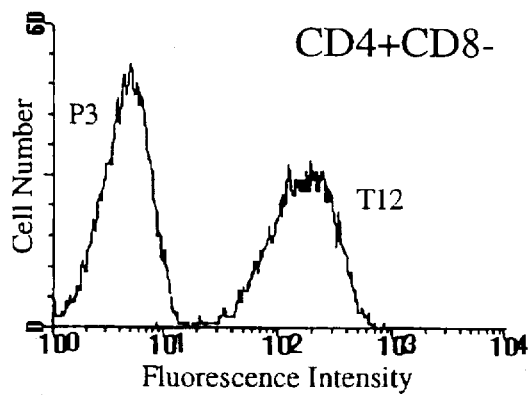
Figure 18D:
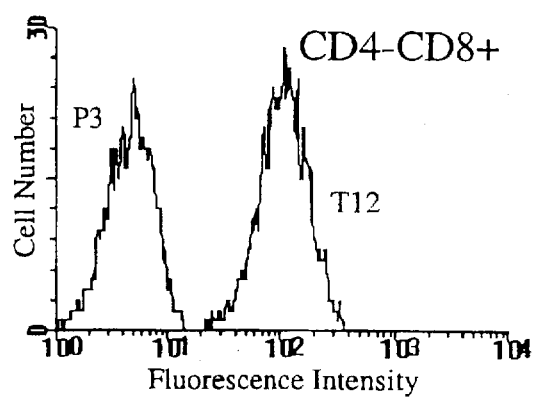

FIG. 17. Binding of COS-CD6 to TE cells is CD6-specific. Shown are histograms of CD6 expression on COS-neo (control) cells and COS-CD6 cells as determined by indirect immunofluorescence with mAb T12 and flow cytometry. Background fluorescence (control mAb P3) is depicted by a dotted line and CD6 expression is indicated by a solid line. The bar graph depicts COS-neo and COS-Cd6 binding to TE cells in the presence of either mAbs P3 or T12. Shown are the mean and SEM of three separate experiments.

FIG. 18. Expression of CD6 on thymocyte subsets. Thymocytes were stained with mAb T12, fluorescein conjugated Fab fragments of goat anti-mouse IgG and a combination of CD4-PE and CD8-cychrome and analyzed on a FACStar$^{Plus}$ flow cytometer. Shown are data representative of experiments on 3 different thymuses with histograms of CD6 expression on all thymocytes, CD4+CD8+(immature, DP) thymocytes, CD4+CD8- (mature, SP4) and CD4-CD8+ (mature, SP8) thymocytes. Background fluorescence (with control mAb P3) is shown in each histogram.

Figure 19:
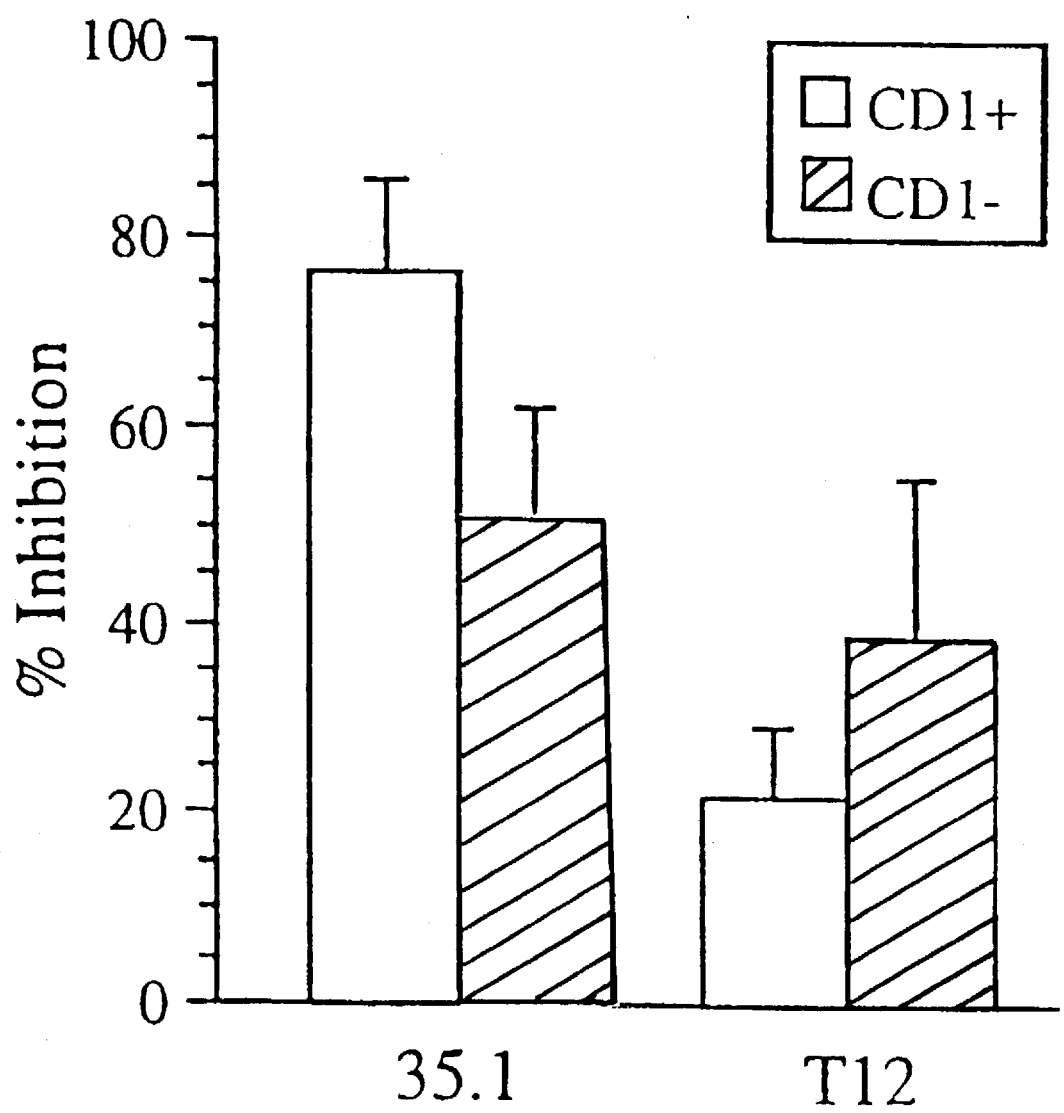

FIG. 19. CD6 mediates the binding of both mature and immature thymocytes to TE cells. CD1+or CD1-thymocytes were incubated with TE cells in the presence of either control antibody (P3), anti-CD2 (35.1) or anti-CD6 (T12 and assayed for rosette formation. The average percentage inhibition of TE-thymocyte binding and SEM (relative to control antibody) by anti-CD2 and anti-CD6, from 3 separate experiments, is shown. Inhibition of CD1+(immature) thymocyte binding to TE cells is depicted by open boxes and inhibition of CD1- (mature) thymocyte binding is depicted by filled boxes. The binding of both the mature and immature subsets of thymocytes to TEC is inhibited by anti-CD2 and anti-CD6 antibodies. The difference in inhibition of CD1+vs. CD1- cells by anti-CD2 mAb 35.1 was statistically significant ($p<0.01$) but the difference in inhibition by anti-CD6 mAb T12 was not ($p<0.25$).

FIG. 20. Thymic epithelial cells and thymic fibroblasts express a trypsin-sensitive surface ligand for CD6. (A) Shown are representative histograms depicting the reactivities with Cd6-Rg of thymic epithelial cells, thymic fibroblasts, and thymocytes. Also shown in each panel are background levels of fluorescence with control fusion protein CD5-Rg. (B) The binding of CD6-Rg to TE cells in either divalent cation containing media (-EDTA), trypsin-treated TE cells in media (trypsin) or TE cells in PBS+10 mM EDTA (EDTA) was tested. Shown are histograms of a representative experiment (from >10 performed) depicting CD6-Rg binding to TE cells as determined by indirect IF and flow cytometry.

FIG. 21. Effect of preincubation of J4-81 and J3-119 on CD6-Rg binding to TE cells. Shown are histograms of CD6-Rg binding to the surface of human TE cells, as detected by indirect IF and flow cytometry, in the presence of mAbs P3 (control), J4-81 or J3-119 in media containing divalent cations (-EDTA) or no divalent cations (+EDTA). The binding of control human IgG is shown in each panel. The bottom panels show composite summary histograms of CD6-Rg binding in the presence of either P3, J4-81 or J3-119. Data are representative of 10 experiments in the presence of divalent cations and 2 experiments with no divalent cations.

FIG. 22. MAb J3-119 blocks the binding of biotinylated J4-81 to the surface of TE cells. Shown is the specific binding of biotinylated J4-81 (in fluorescence units minus background) in the presence of increasing concentrations of mAbs A3D8J3-119 and J4-81. Diluted ascites (1:50, 1:100, 1:250 and 1:500) was used and relative amount of mAb is presented as the inverse of the dilution$\times 10^3$. MAb A3D8, which binds strongly to the surface of TE cells did not alter the binding of J4-81 while both J3-119 and non-biotinylated J4-81 inhibited the binding of biotinylated J4-81. Data are representative of 2 experiments.

Figure 23:
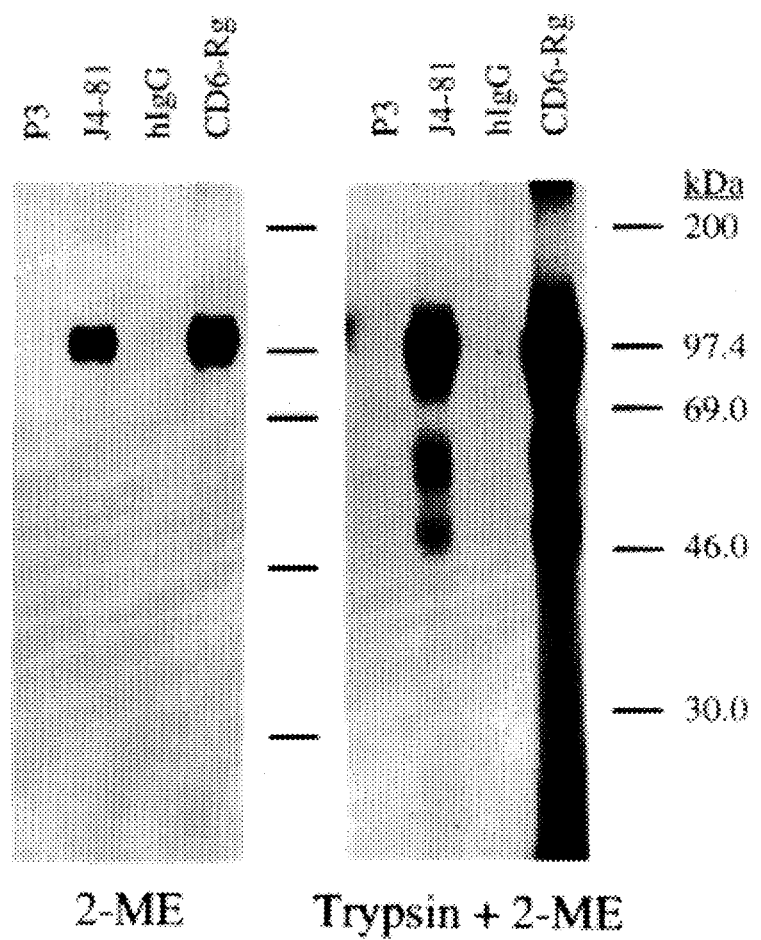

FIG. 23. MAb J4-81 and CD6-Rg bind to the same 100 kDa glycoprotein on the surface of human TE cells. Shown are autoradiographs of $^{125}$I-labelled TE cell surface proteins cross-linked to either mAb P3 (control), mAb J4-81, hIgG1 (human Fc control), or CD6-Rg. The cross-linked proteins were treated with either 2-ME alone (to cleave the cross-linker) or trypsin and 2-ME prior to electrophoresis. Both CD6-Rg and mAb J4-81 bound to 100 kDa proteins with identical trypsin digestion patterns. Data are representative of 2 separate experiments.

Figure 24:
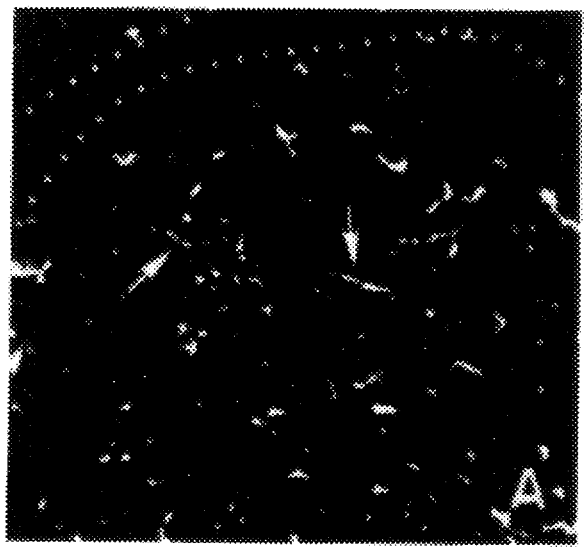
Figure 24:
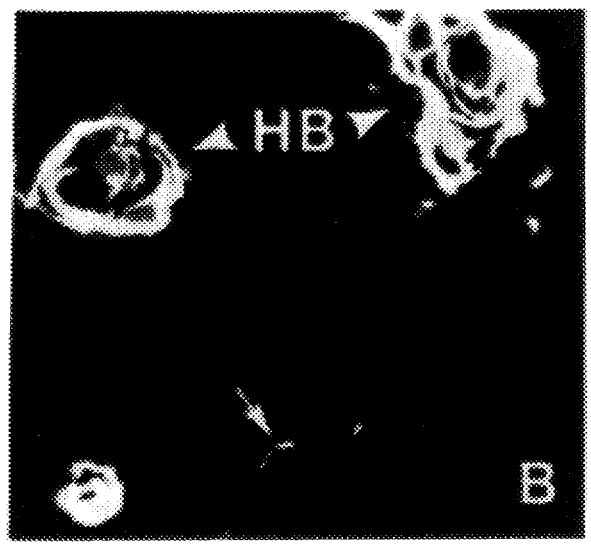

FIG. 24. Expression of CD6L-100 in postnatal human thymus. Shown are photomicrographs (representative of experiments on 5 thymuses) of frozen sections of 2 month human thymus stained by indirect IF with mAb J4-81. Panel A shows a section of thymus stained by indirect IF with mAb J4-81. Panel A shows a section of thymus cortex and panel B shows a section of thymus medulla with Hassall's bodies (HB). The thymic capsule is indicated by dashed lines in panel A. Thymic epithelial cells (arrows), in both the cortex and in and around HB in medulla, reacted with mAb J4-81. Thymocytes did not react with mAb J4-81. An identical pattern was seen using mAb J3-119 (not shown) (400× magnification).

DETAILED DESCRIPTION OF THE INVENTION

The present invention relates to a molecule that represents one member of a binding pair, the other member of that pair being the CD6 molecule present on the surface of mature thymocytes, peripheral T cells and a subset of B cells. The CD6 ligand, as it is referred to herein, occurs in two forms—one form is independent of divalent cations for CD6 binding, the other is divalent cation-dependent. The first of these forms comprises a 35 kDa protein and a 105 kDa protein (as determined by SDS-PAGE under reducing conditions). The second form comprises a 90 kDa protein (determined by SDS-PAGE under reducing conditions).

The CD6 ligand of the invention is present on a variety of tissue and cell types, including fibroblasts, skin epidermal keratinocytes, medullary TEC, gut epithelium, pancreas islet and acinar cells, as well as monocytes and activated T cells, hepatocytes and neurons of the brain cortex. The tissue distribution of the CD6 ligand indicates that the CD6/CD6 ligand system is important for mediation of T cell interactions with monocytes and other activated T cells as well as with epithelial cells, fibroblasts and specialized cells, such as pancreatic islet cells.

The CD6 ligand of the invention can be isolated from natural sources (see above) by immunoprecipitation, for example, with a CD6 fusion protein as described in the Example that follows. A suitable fusion protein, the CD6-Ig (=CD6-Rg) fusion protein, can be produced by ligating the coding sequence of the extracellular portion of CD6 (Aruffo et al, J. Exp. Med. 174:949 (1991)) to the coding sequence of the Fc portion of human IgG as described by Seed and Aruffo (Proc. Natl. Acad. Sci. USA 84:3365 (1987)). The CD6-Ig fusion protein can be expressed in COS cells by transient transfection as previously described (Seed and Aruffo, Proc. Natl. Acad. Sci. USA 84:3365 (1987)).

The availability of the CD6 ligand from cell sources, including those noted above, makes possible the cloning of the CD6 ligand gene(s). Sequencing of all or part of the CD6 ligand will provide the information necessary for designing nucleic acid probes or primers suitable for use in isolating the CD6 ligand coding sequence(s), for example, from cDNA or genomic DNA libraries. The Unizap XR system from Stratagene can be used to prepare a suitable cDNA library from thymic epithelial cells. Other libraries that can be used include the brain frontal cortex and liver tumor Hep G2 cDNA libraries from Stratagene.

More specifically, the CD6 ligand can be purified by affinity chromatography. Anti-CD6 ligand mab (5–10 mg) (see, for example, Pesando et al, J. Immunol. 137:3689 (1986)) can be used to prepare an affinity column for CD6 ligand by immobilization of anti-CD6 ligand on CNBr-activated Sepharose 4B (Pharmacia), as described by Patel et al (Virology 149:174 (1986)). CD6 ligand from protein lysates of, for example, thymic epithelial cell or B cell line lysates, can be affinity purified using the anti-CD6 ligand Sepharose column. CD6 ligand can be further purified over a $C_{18}$ reverse phase HPLC column (Vydac) using acetonitrile/$H_2O$ gradients containing trifluoroacetic acid with UV detection at 240nm. Once purity has been established, the N-terminal amino acid sequence of intact CD6 ligand, and peptides generated with V8-protease, trypsin or other proteases, can be determined. From the amino acid sequence, degenerate oligonucleotide primers can be designed that recognize cDNA for CD6 ligand, to PCR amplify CD6 ligand cDNA. To guard against errors in the PCR amplification, $^{32}$P-labelled PCR amplified CD6 ligand cDNA can be used as a probe to detect CD6 ligand cDNAs from an appropriate cDNA library. The nucleotide sequence of CD6 ligand cDNA can be determined using standard methodologies. (See generally, Sambrook, Fritsch and Maniatis, Molecular Cloning: A Laboratory Manual, 2nd Edition, Cold Spring Harbor Laboratory Press (1989).)

Once cloned, the CD6 ligand encoding sequence can be introduced into an expression construct. Such a construct comprises a vector (eg, viral or plasmid) and the CD6 ligand encoding sequence operably linked to a promoter. The construct can be used to transform a procaryotic or eucaryotic host cell. Eucaryotic hosts are preferred since the CD6 ligand is a glycosylated protein. Mammalian cell systems are particularly advantageous (eg, the COS M6 system). The CD6 ligand can be produced in soluble form by culturing the transformed hosts under conditions such that the encoding sequence is transcribed and that transcript is translated into protein.

The present invention relates to the CD6 ligand in its entirety and also to portions thereof suitable, for example, for use as antigens that can be used in standard immunization protocols to generate antibodies (monoclonal or polyclonal) (or binding fragments thereof) specific for the CD6 ligand. Such portions represent at least 5 consecutive amino acids of the CD6 ligand, preferably, at least 10 amino acids, more preferably, at least 25 consecutive amino acids, most preferably at least 50 amino acids. Larger portions can also be used, for example, portions of at least 100, 250 or 500 amino acids.

Ligation of CD6 on T cells by anti-CD6 mab provides a potent co-mitogenic signal for unseparated T cells (Gangemi et al, J. Immunol. 143:2439 (1989); Morimoto et al, J. Immunol. 140:2165 (1988); Wee et al, J. Exp. Med. 177:219 (1993)), directly activates separated CD4+T cell clones (Swack et al, J. Biol Chem. 266:7137 (1991)), and directly activates TCRγδ but not TCRαβ T cells (Pawlec et al, Hum. Immunol. 31:165 (1991)). Thus, CD6 is a molecule of mature T cells that is intimately involved in TCR mediated T cell triggering; ligation of the TCR complex leads to CD6 phosphorylation (Wee et al, J. Exp. Med. 177:219 (1993)). Methods of inhibiting CD6/CD6 ligand interactions in vivo provides a potent immunotherapeutic strategy.

Soluble CD6 ligand (isolated from natural sources or produced recombinantly) can be used, for example, to inhibit CD6-mediated T cell activation that is dependent on T cell CD6-CD6 ligand+ accessory cell contact. Such an immunotherapeutic regimen is useful in treating diseases caused by activated T cells such as multiple sclerosis, inflammatory uveitis, including Cogan's syndrome, rheumatoid arthritis, T cell mediated vasculitis syndromes, such as Wegener's granulomatosis and temporal arteritis, and organ allograft rejection. Indeed, it has been-shown that CD6 mab depletion of bone marrow (BM) used for allogeneic BM transplant prevents graft versus host disease (Soiffer et al, J. Clin. Oncol. 10:1191 (1992)).

In addition to soluble CD6 ligand, soluble CD6, as well as mimetopes (mimics) of CD6 and CD6 ligand (prepared, for example, as described by Szostak (TIBS 17:89 (1992)) or Tsai et al (J. Immunol. 150:1137 (1993)), for example, from random RNA, DNA or peptide libraries), can be used as immunotherapeutic agents in regimens involving inhibiting CD6/CD6 ligand interaction. Anti-CD6 and anti-CD6 ligand antibodies (preferably monoclonal antibodies) can also be used in such regimens. These immunotherapeutic agents can be formulated with, for example, a pharmaceutically acceptable carrier, diluent, etc., as a pharmaceutical composition. The concentration of active agent in the composition and the amount of active agent adminstered will vary with the agent, the patient and the effect sought. Optimum doses can be readily determined.

Certain aspects of the invention are described in greater detail in the non-limiting Examples that follows.

EXAMPLE I

Experimental Details

Cells and Culture Conditions.

TEC were cultured by the explant technique in enriched media as previously described (Singer et al, Human Immunol. 13:161 (1985)). Human thymus tissue was obtained from the Department of Pathology, Duke University Medical Center, as discarded tissue from children undergoing corrective cardiovascular surgery. Contaminating thymic fibroblasts were removed by complement mediated lysis with mAb 1B10 which binds to a cell surface antigen on human fibroblasts (Singer et al, J. Invest. Dermatol. 92:166 (1989)) followed by treatment with 0.02% EDTA in PBS. 3T3 fibroblast feeder layers were removed by treatment with 0.02% EDTA in PBS prior to detachment of TEC from culture dishes with 0.05% trypsin in PBS containing 0.02% EDTA. Cells were washed 3 times prior to analysis. TEC were activated with 500 U/ml IFN-γ in DMEM containing 5% FCS, 1 mM sodium pyruvate (Gibco) 0.025 µg/ml amphotericin B (Gibco), 100 U/ml penicillin and 1000 µg/ml streptomycin for 48–72h at 37° C.

Thymocytes were obtained by teasing from thymus tissue purified by centrifugation through ficoll-hypaque and washed with RPMI 1640. Thymocytes were used immediately or frozen in media containing 20% FCS, 7.5% DMSO and 10 µg/ml gentamicin (Scherring) in RPMI 1640. Frozen thymocytes were thawed by incubation in media containing 30% FCS, 10 µg/ml deoxyribonuclease I (Sigma), 10 µg/ml gentamicin and 20 U/ml heparin (Upjohn) in RPMI 1640 as described (Denning et al, J. Immunol. 138:680 (1987)). Viable thymocytes were purified by centrifugation through ficoll-hypaque.

COS-M6 cells (ATCC) were grown in DMEM containing 10% FCS, 1 mM sodium pyruvate (Gibco), 0.025 µg/ml amphotericin B (Gibco), 100 U/ml penicillin and 100 µg/ml streptomycin.

Human epidermal keratinocytes (EK) were cultured from neonatal foreskins. Foreskins were incubated at 25 40C. overnight in 2.5 mg/ml trypsin type III (Sigma) in HBSS (GIBCO), the epidermis was removed, teased into a single cell suspension, seeded onto mitomycin C treated 3T3 fibroblast feeder layers and cultured as described (Hashimoto et al, J. Exp. Med. 157:259 (1983)).

Detection of Cell Surface Antigens:

Unfixed cultured cells were suspended in either PBS, TBS (0.9M NaCl 50 mM Tris-HCl, pH 7.3) or DMEM containing 2% BSA and 0.1% NaN$_3$. Cells were incubated with CD6-Rg, CD5-Rg or ELAM-Rg (from Sandro Aruffo, Bristol-Myers Squibb), recombinant fusion proteins (100 µg/ml) for 30 min at 4° C. and washed with PBS containing 2% BSA and 0.1% NaN$_3$. FITC conjugated goat anti-human IgG$_1$ was used as a secondary reagent. Cells were analyzed on a FACStar Plus flow cytometer (Becton-Dickinson, Inc., Mountain View, California) and data was processed using the software program PC-Lysys (Becton-Dickinson).

TEC-Thymocyte Rosette Binding Assay:

TEC-thymocyte rosette binding assays were performed as described (Singer et al, Proc. Natl. Acad. Sci. USA 83:6588 (1986)). Briefly, $10^6$ thymocytes were mixed with $2 \times 10^5$ TEC in PBS or DME containing 2% BSA and 0.1% NaN$_3$, centrifuged for 3 min at 250 g, and incubated for 60 min at 4° C. Cells were gently resuspended and counted under light microscopy. TEC which bound 3 or more thymocytes were scored as positive. The thymocytes used in these experiments were either freshly isolated, thawed from liquid nitrogen, or separated into subpopulations. Thymocytes were separated into CD1$^+$(immature, CD6$^{low}$) or CD1$^-$ (mature, CD6$^{hi}$) subpopulations by indirect immunofluorescent staining with Na1/34 (anti-CD1; from Andrew McMichael, Oxford, England) and goat anti-mouse IgG (KPL) followed by fluorescence activated cell sorting using a FACStar Plus. All thymocyte subpopulations were >95% pure on reanalysis of sorted cells. TEC-thymocyte binding was inhibited by preincubation of either thymocytes or TEC with antibodies or fusion proteins prior to binding. Antibodies used were: P3×63 (control mab) (ATCC), 35.1 (anti-CD2; from John Hansen, Seattle, Washington (Martin et al, J. Immunol. 131:180 (1983)) and T12 (anti-CD6; from Ellis Reinherz, Boston, Mass. (Reinherz et al, Cell 30:735 (1982) ).

COS Cell Transfection and Binding Studies:

Stable lines of CD6-expressing COS cells were made by co-transfection of plasmids containing the CD6 gene under the control of the CMV promoter (A. Aruffo, Seattle, Wash. Aruffo et al, J. Exp. Med. 174:949 (1991)) and the pSVneo plasmid containing the bacterial neomycin resistance gene driven by an SV40 promter as described by Liao et al (J. Immunol. Dec. 1, 1993). Cells expressing the neomycin resistance gene were selected by incubation in DME/ 10%FCS containing 60µg/ml G418 (GIBCO). Cells expressing CD6 were identified by indirect immunofluorescence using mab T12. CD6 positive and negative cells were cloned by single cell sorting using a Becton-Dickinson FACStar$^{Plus}$ flow cytometer.

CD6-expressing COS cells (COS-CD6D) and control COS cells (COS-Neo) were used in binding studies, with TE cells similar to those outlined above. To differentiate between COS cells and TE cells, TE cells were metabolically labelled with 1 µg/ml calcein AM (Molecular Probes, Eugene, Oregon) for 15 min at 37° C. in PBS prior to harvest. Calcein AM-labelled cells are fluorescent and can be easily differentiated from other cells by fluorescence microscopy.

Construction of the CD6-Rg (CD6-Ig) Chimeric Gene and Preparation of the Fusion Protein:

The CD6 immunoglobulin fusion gene was constructed by digesting a plasmid containing the cDNA encoding the full-length CD6 (Aruffo et al, J. Exp. Med. 174:949 (1991)) with the restriction enzyme Esp1. The Esp1 digested plasmid was then flushed with DNA polymerase and the appropriate Bam HI linkers were added to it. The plasmid was then digested with Bam HI and Nde 1. The fragment that contained the extracellular domain of CD6 was then isolated and subcloned into a vector containing a cDNA fragment encoding the constant domain of a human IgG1 protein (Aruffo et al, Proc. Natl. Acad. Sci. USA 89:2292 (1992)). The constructions of CD5-Ig and CTLA4-Ig have been described elsewhere (Linsley et al, Science 257:792 (1992) and J. Exp. Med. 174:561 (1991)). 500 µg of DNA of the appropriate gene was transfected into COS cells by the DEAE-dextran chloroquine method. 18–24 hrs later, the 10% FBS Dulbeco's modified Eagle's medium was replaced by serum-free media after a rinse wash with PBS. The cell culture was maintained 7–10 days before it was harvested. Briefly, the supernatant containing the fusion protein was centrifuged at 2500 rpm for 20 min and filtered through a 0.45 µm Millipore filter. The supernatant was passed over a 2-ml packed Protein A column at a flowrate of 1.00 ml/min. The bound fusion protein was eluted with pH 3.5, 0.1M citric acid and was immediately neutralized with pH 9.0, 1.0M Tris. The eluted protein was then dialyzed overnight in PBS and protein determination was done using the Bradford method.

Screening of Mabs for Inhibition of CD6-Ig Binding to TE Cells:

Mabs from the 5th International Workshop on Human Leukocyte Differentiation Antigens and a panel of anti-integrin mabs (see description of FIG. 4) were screened for reactivity to the surface of TE cells as outlined above, using fluorescein-conjugated goat anti-mouse IgG (KPL) as a secondary reagent. Of the 154 mabs that reacted to TE cells, 126 were used in this assay. TE cells (100k) were incubated with ascites or purified mab at 1:100 for 15 min at 4° C. Either CD5-Ig or CD6-Ig (5 µg) was added to this mixture and allowed to react for 2 hr at 4° C. After washing with PBS-containing 2% BSA, CD5-Ig and CD6-Ig were labelled with a fluorescein conjugated goat antiserum specific for the Fc protein of human IgG (Sigma). This reagent did not cross react with most murine mabs. To account for any cross-reactivity that may have occurred, binding was determined to be the difference in fluorescence (ΔFL) between samples containing CD6-Ig and CD5-Ig. The ΔFL of samples preincubated with control mab P3 was considered to represent 100% binding.

Immunoprecipitation and Protein Labelling Conditions:

120 µCi/ml glucosamine (NEN) was used in the labelling experiment. The cells were cultured in glucose-free media plus 10% dialyzed fetal calf serum for 48 hrs upon addition of the radiolabelled glucosamine. The cells were then lifted with EDTA, washed in HBSS and lysed in 20 mM Tris, pH 7.5 containing leupeptin, PMSF and pepstain (1 µg/ml), 0.05% sodium cholate, 2% NP-40. The lysate was pre-cleared with 100 µg/ml human IgG1 followed by 50 µl of Protein A beads. Pre-cleared lysates were then incubated with 50 µg/ml CD6-Rg or CTLA4-Ig or 2 µg/ml anti-EGF receptor antibody. 2 mM Ca++ and Mg++ were added to the lysates (this is the concentration of divalent cations contained in the HBSS binding buffer). The immunoprecipitates were washed 3× in lysis buffer, 2× in PBS, boiled in reducing SDS-PAGE loading buffer and loaded unto a 8-10.5% SDS-PAGE gel. The gels were fixed in 40% propanol, enhanced in m AMiAmplify$^R$ reagent (Amersham), dried and autoradiographed.

Results

Anti-CD6Mabs and CD6-Ig Fusion Proteins Inhibit TE-thymocyte Binding:

Using a suspension TE-thymocyte binding assay (Table 1), it was found that the CD6 mab T12 inhibited TE-thymocyte binding by 49±9% (N=5). Similarly, recombinant CD6-Ig fusion protein inhibited TE-thymocyte binding by 35±9% (N=5). This suggested that human TEC express a ligand for CD6.

TABLE 1

Effect of monoclonal antibodies and fusion protein on thymocyte-thymic epithelial cell binding

| mab/fusion protein | % Binding[a] | % Inhibition[b] |
|---|---|---|
| P3 | 32.8 ± 5.2 | 0 |
| 35.1 (anti-CD2) | 8.2 ± 2.4 | 76.0 ± 5.4 p<0.003 |
| T12 (anti-CD6) | 17.2 ± 3.8 | 48.7 ± 9.2 p<0.015 |
| ELAM-IG | 29.7 ± 3.6 | 0 |
| CD6 | 19.3 ± 3.2 | 34.5 ± 9.3 p<0.05 |

[a]Binding was determined to be the percentage of TE cells rosettes (≥3 bound thymocytes). Shown is the mean and standard error of 5 separate experiments.
[b]% Inhibition = 100 (Binding$_{control}$ − Binding$_{exp}$)/Binding$_{control}$. The controls were P3 for mabs, and ELAM-Ig for CD6-Ig.
p values represent 2 tailed Student's t-test comparing binding in the presence of mabs or CD6-Ig to control binding.

Figure 1:
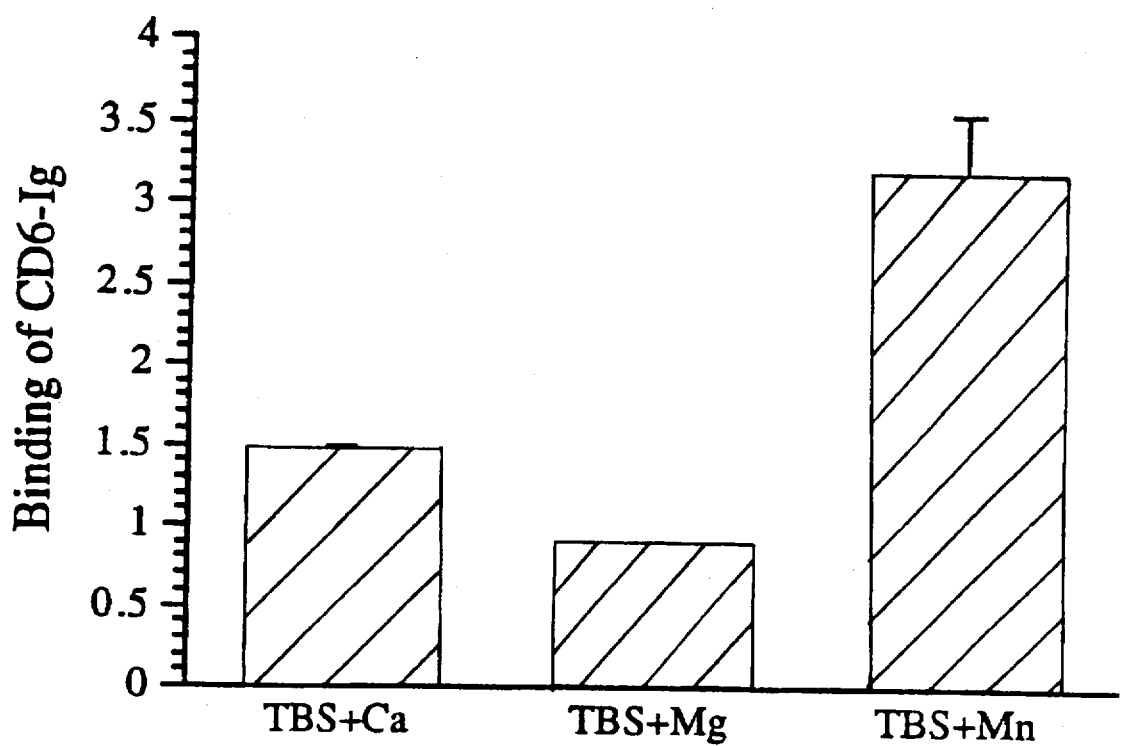
FIG. 1. Effect of divalent cations on binding of CD6-Ig (=CD6-Rg) to thymic epithelial cells (TEC). TEC were incubated with 5 µg of CD6-Ig or CD5-Ig in buffers containing 2% BSA, Tris-HCl buffered saline (TBS) and either 5 mM $CaCl_2$, 5 mM $MgCl_2$ or 5 mM $MnCl_2$, and assayed by indirect immunofluorescence and flow cytometry. Shown is the relative binding of CD6-Ig in the various buffers. Relative binding was determined as the ratio of specific binding of CD6-Ig (fluorescence of CD6-Ig -fluorescence of CD5-Ig) in sample buffer to the specific binding in TBS. Shown is a representative of three experiments (except for TBS+Mg which was performed only once). Both $CaCl_2$ and $MnCl_2$ were able to significantly enhance the binding of CD6-Ig to TEC ($p \leq 0.1$).
Figure 2:
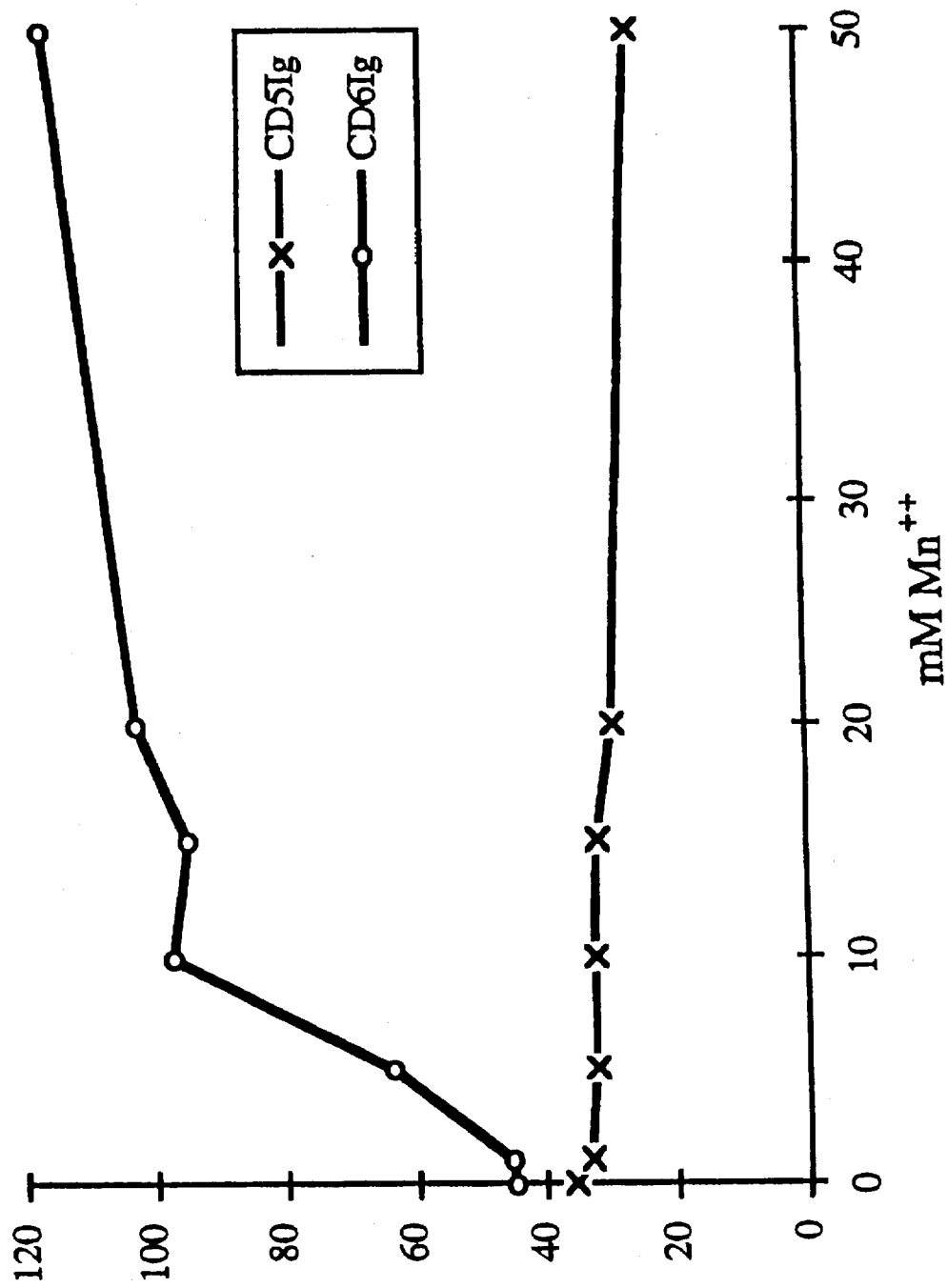
FIG. 2. CD6-Ig binding to TEC is enhanced by $Mn^{++}$. TEC were incubated with 5 µg of CD6-Ig or CD5-Ig in buffers containing 2% BSA, TBS and various concentrations of $MnCl_2$, and assayed by indirect immunofluorescence and flow cytometry. The graph shows the relative binding of CD6-Ig in buffers containing varying amounts of $MnCl_2$. Shown is a representative of three separate experiments.

Human TE cells express a ligand for CD6:

To confirm that human TEC express a ligand for CD6, TEC were incubated with recombinant CD6-Ig fusion proteins and assayed for CD6-Ig binding to TEC by indirect immunofluorescence followed by flow cytometry. Neither of the negative controls (CD5-Ig and ELAM-Ig) bound to the surface of TEC while CD6-Ig did bind to TE cells (Table 2), indicating that there is a ligand for CD6 expressed on the surface of human TE cells. CD6-Ig binding to the CD6 ligand on TE cells was enhanced by divalent cations (Ca$^+$ +and Mn$^{++}$) and partially inhibited by EDTA (FIGS. 1 and 2). The data suggest that there are at least two components to the binding of CD6-Ig to TEC — a component (or ligand) that is dependent upon divalent cations, and a component (or ligand) that is divalent cation-independent.

TABLE 2

Reactivity of fusion proteins on human thymic epithelial cells[a]

| fusion protein | MFC[b] |
|---|---|
| IgG$_1$ | 72.9 |
| ELAM-Ig | 70.5 |
| CD5-Ig | 72.1 |
| CD6-Ig | 164.9 |

[a]Cultured TE cells were incubated with 2000 µg/ml fusion proteins. Fusion proteins were detected by indirect immunofluorescence followed by flow cytometry.
[b]Linear Mean Fluorescence Channel. Data are representative of 3 experiments.

Figure 3:
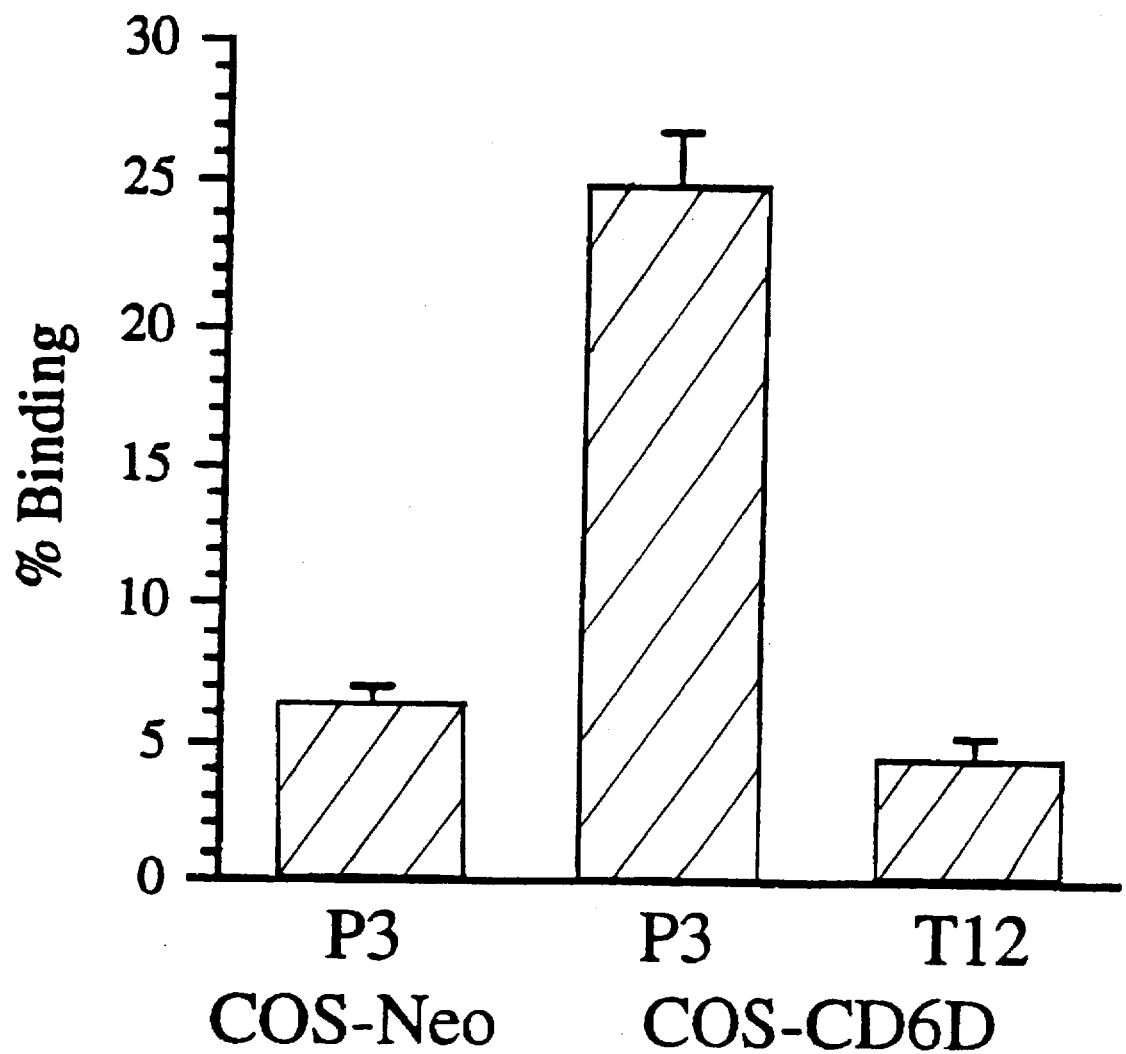
FIG. 3. Binding to TEC is enhanced by the expression of CD6 in COS cells. COS cells that express CD6 in a stable manner (COS-CD6D) or control COS cells (COS-Neo) were incubated with calcein-AM labelled TEC at a ratio of 1:5 for 60 min at 4° C. Binding was detected by using a combination of light and fluorescence microscopy. Binding was determined to be the percentage of COS cells with 3 or more bound TEC. The expression of CD6 in COS cells enhanced the binding of COS cells to TEC, and this binding was inhibited by anti-CD6 antibody.

CD6 Is an Adhesion Molecule:

The fact that T12 and CD6-Ig both partially inhibit the binding of thymocytes to TEC strongly suggested that CD6 was an adhesion molecule. The TE rosette studies, however, did not rule out the possibility that T12 and CD6-Ig inhibited TE-thymocyte binding because of steric hinderance. To determine if CD6 was indeed an adhesion molecule, a COS cell line (COS-CD6D) was made that expressed high levels of transfected CD6. COS cells without CD6 (CS-Neo) did not bind to TEC, whereas COS-CD6D cells did bind TEC (FIG. 3). Furthermore, this COS-CD6D:TE cell binding was CD6-dependent as binding was inhibited by mab to CD6 (T12).

Figure 4:
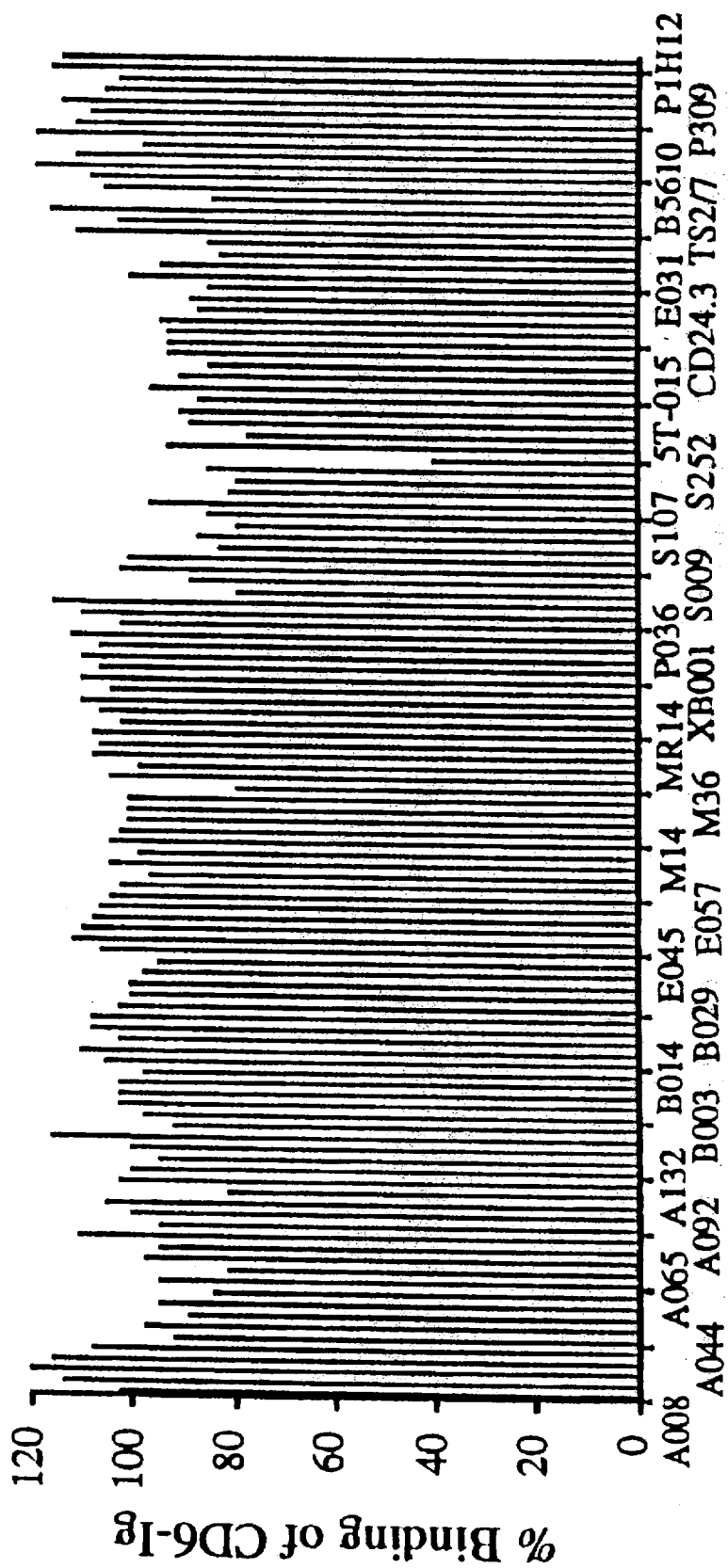
FIG. 4. Monoclonal antibody J4-81 inhibits the binding of human CD6-Ig fusion protein to human TEC. The binding panel of 470 mabs from the V International Workshop on Human Leukocyte Differentiation Antigens and a panel of anti-integrin mabs was screened for reactivity to TE cells. Of the 154 mabs that reacted with TE cells, 126 were used in assays to inhibit the binding of CD6-Ig to TE cells. The workshop mabs that reacted with TE cells and were used in this study were: A008, A014, A023-4, A036-7, A044, A047-

Mab J4-81 Reacts With A Ligand For CD6:

To identify the CD6 ligand, a large panel of anti-integrin mabs and a blind panel of 479 mabs from the Vth International Workshop on Human Leukocyte Differentiation Antigens were screened for reactivity to TE cells. Of the 154 mabs that reacted with TEC, 126 mabs were used in assays to inhibit the binding of CD6-Ig to TEC. As shown in FIG. 4, only Workshop mab S252 (J4-81) was able to inhibit the binding of CD6-Ig to TEC. Mab J4-81, which was raised against B cell surface antigens, recognizes a 105 kDa protein on B cells (Pesando et al, J. Immunol. 137:3689 (1986)) and reacts strongly with the surface on all cultured TEC (FIG. 5) and with medullary TEC in frozen sections of human thymus (FIG. 6).

Immunoprecipitation of 105 kDa, 90 kDa and 35 kDa Molecules from TEC with CD6-Ig:

In the absence of EDTA, CD6-Ig fusion protein immunoprecipitated protein species with molecular weights of 105, 90 and 35 kDa (FIG. 7, lane 1) (note approximately 150 kDa band). In the presence of EDTA, CD6-Ig immunoprecipitated only the 105 and 35 kDa species (FIG. 7, lane 2) (note approximately 150 kDa band). In lane 3, in the absence of EDTA, the control fusion protein, CTLA4-Ig, did not immunoprecipitate the 105, 90 or 35 kDa protein species.

Mab J4-81 Inhibits the Binding of TE Cells to COS-CD6D Cells:

A third approach has been used to define that the 105/35 kDa protein molecules detected by mab J4-81 is a ligand for CD6. As shown above, COS-CD6D:TEC binding is CD6-specific. To further demonstrate that CD6 and the 105/35 kDa molecules recognized by J4-81 form an adhesion molecule pair, COS-CD6D:TEC binding with mab J4-81 was inhibited (Table 3).

TABLE 3

Effect of monoclonal antibodies COS-CD6D:TEC binding

| mab | % Binding[a] | % Inhibition[b] |
|---|---|---|
| P3 | 25.0 ± 1.8 | 0 |
| T12 (anti-CD6) | 4.5 ± 0.7 | 82.7 ± 2.1 p<0.0007 |
| S252 (J4-81) | 8.7 ± 0.7 | 65.3 ± 1.8 p<0.0008 |

[a]Binding was determined to be the percentage of COS cells rosettes (≧3 bound TEC). Shown is the mean and standard error of 3 separate experiments.
[b]% Inhibition = 100 (Binding$_{p3}$ − Binding$_{exp}$)/Binding$_{p3}$.
p values represent 2 tailed Student's t-test comparing inhibition in the presence of T12 or J4-81 inhibition in the presence of P3.

Reactivity of J4-81Mab with Human Tissue in Indirect IF Assay:

Mab J4-81 reacted with TEC, epidermal keratinocytes, fibroblasts, acinar cells and islets cells of pancreas, gut epithelium, monocytes (10%) and activated PB T cells (21%). B cells are also positive for J4-81 (Pesando et al, J. Immunol. 137:3689 (1986)). Taken together, these data demonstrate that the CD6-CD6 ligand system is involved in TEC-thymocyte interactions, that CD6 is an adhesion molecule and that 105/35 kDa proteins detected by mab J4-81 comprise a ligand for CD6. Moreover, that the CD6-divalent cation-independent ligand defined by mab J4-81 is expressed on a wide variety of immune and epithelial cell types suggests that the CD6/CD6 ligand system is important in immune cell interactions with other immune cells and with a wide variety of epithelial microenvironments.

EXAMPLE II

Experimental Details

Cell Lines, Fusion Protein, and Antibodies.

The colon carcinoma-derived cell line H3719 and the melanoma-derived cell line H3606 were from Drs. K. E. and I. Hellstrom (Bristol-Myers Squibb, Seattle, WA). The human breast epithelial cell line HBL-100, the EBV-transformed human B cell line LCL, the human lung fibroblast IMR90, the adult T cell leukemia Jurkat, the cutaneous T cell lymphoma HUT78, the human peripheral blood acute leukocytic leukemia derived cell line HPB-All, the human T cell lymphoma H9, the human Burkitt lymphoma Raji, the fibroblast cell line GM0833, the B cell lymphoblastoma Peer, the T cell leukemia JM, and the B cell lymphoblastoma LTR228 were used and obtained primarily from the American Type Culture Collection (Rockville, MD). The CD5-Rg (Aruffo et al, Proc. Natl. Acad. Sci. USA 89:10242 (1992)), ELAM1-Rg (Walz et al, Science 250:1132 (1990)), and CTLA4-Ig (Linsley et al, J. Exp. Med. 174:561 (1991)) have been previously described. The anti-CD6 mAb G3-6 (IgG) was from Dr. J. Ledbetter (Bristol-Myers Squib, Seattle, Wash.) (Ledbetter et al, Proc. Natl. Acad. Sci. USA 84:1384 (1987)); the anti-CD6 mAb MBG6 (IgM) was from Dr. A. McMichael (Oxford University, Oxford, U.K.) (Bastin et al, J. Clin. Exp. Immunol. 46:597 (1981)); the anti-CD6 mAb 2H1 was from Dr. C. Morimoto (Dana-Farber Cancer Institute, Boston, Mass.) (Morimoto et al, J. Immunol. 140:2165 (1988)); the anti-CD6 mAbT12 has been previously described (Reinherz et al, Cell 30:735 (1982)). The DNA restriction enzymes and the DNA linkers were obtained from New England Biolabs (Beverly, Mass.); RPMI, HBSS, FBS, and prestained molecular weight markers were obtained from GIBCO-BRL (Gaithersburg, Md). Human epidermal keratinocytes (EK) were cultured from neonatal foreskins. Foreskins were incubated at 4° C. overnight in 2.5 mg/ml trypsin type III (Sigma, St. Louis, M.) in HBSS (GIBCO-BRL), the epidermis was removed, teased into single-cell suspension, seeded onto mitomycin C-treated 3T3 fibroblast feeder layers, and cultured as described (Hashimoto et al, J. Exp. Med. 145:259 (1983)).
Preparation of CD6-Rg.

The plasmid encoding the CD6-Rg containing a full-length cDNA clone encoding CD6 (Aruffo et al, J. Exp. Med. 174:949 (1991)) was digested with the restriction enzyme EspI, treated with the Klenow fragment of DNA polymerase I, and ligated to BamHI linkers (New England Biolabs, Beverly, Mass.). The vector was then digested with the restriction enzymes NdeI and BamHI. The NdeI/BamHI DNA fragment containing the extracellular domain of CD6 was subcloned into a plasmid containing a cDNA fragment encoding the constant domains (hinge, CH2, and CH3) of human IgG$_1$. The CD6-Rg protein was prepared by transient expression in COS cells as previously described (Aruffo et al, Cell 61(7):1303 (1990)) and purified from the supernatant of COS cell transfectants by absorption to, and elution from, a protein A column (Repligen, Cambridge, Mass).
CD-6 Rg Cell Binding Studies.

Typically, 5×10$^7$ cells/ml in HBSS/2% FBS/20 mM Hepes (wash/stain buffer) were incubated with 50 µg/ml of fusion protein. Adherent cells were detached from dishes with 0.5 mM EDTA in PBS (PBS/EDTA) and washed once, while nonadherent cells were washed once before incubation with the fusion protein for 1 hr on ice. The cells were subsequently washed three times and incubated with FITC-goat anti-human IgG (10 µg/ml, Tago, Burlingame, Calif.) for 1 hr on ice. The cells were washed three times, fixed with 1% paraformaldehyde in PBS, and analyzed by flow cytometry (Epics V, Coulter, Hialeah, Fla).

This staining procedure was used to examine if the binding of CD6-Rg to HBL-100 cells was saturable. In those experiments the CD6-Rg and control fusion protein were used at the following concentrations: 10, 20, 30, 40, 50, 100, and 200 µ/ml. To investigate the sensitivity of CD6-Rg ligand(s) to trypsin, HBL-100 cells (5×10$^7$) were treated with 0.05% trypsin/0.5 mM EDTA for 30 min at 37° C., washed three times with wash/stain buffer, incubated with CD6-Rg and analyzed by flow cytometry as described above. To examine the divalent cation requirement for CD6-Rg binding, CD6-Rg was incubated with HBL-100 cells in the presence of 15 mM EDTA, or, alternatively, the EDTA was added to HBL-100 cells which had been previously incubated with CD6-Rg and washed. For anti-CD6 blocking experiments CD6-Rg (50 µg/ml) was incubated with a 1:50, 1:100, and 1:200 dilution of the 1 mg/ml anti-CD6 mAb G3-6 (IgG) or ascites containing the MBG6 mAb (IgM, from A. J. McMichael) or an isotype matched (IgM) antibody. To examine the cytokine-induced modulation of CD6-Rg binding to HBL-100 cells, cells were incubated with IL-1β, TNF-α (Genzyme, Boston, Mass.), and IFN-y (Upstate Biotechnology Inc., Lack Placid, N.Y.) (10 ng/ml) individually, in pairwise combinations, or all together, for 48 hr at 37° C., 5% CO$_2$ prior to CD6-Rg binding studies.
Immunoprecipitation Studies.

For immunoprecipitation studies, cells were incubated with 120 µCi/ml of [6-$^3$H]glucosamine (NEN Dupont, Boston, Mass.) in glucose-free RPMI containing 10% normal RPMI and 10% dialyzed FBS for 48 hr at 37° C. and 5% CO$_2$. The cells were lifted from the culture dish with PBS/EDTA, washed in HBSS, and lysed in 20 mM Tris, pH 7.5, containing leupeptin, PMSF, and pepstatin (1 µg/ml, Boehringer Manheim, Indianapolis, IN), 0.05% sodium cholate, 2% NP-40 (lysis buffer). The lysates were spun to remove nuclei and precleared by incubating two times with 50 µg/ml of human IgG1 (Sigma) and 50 µl of protein A-Sepharose slurry (Repligen) for 30 min at 4° C. Cell lysates were then incubated with 50 µg/ml of CD6-Rg or CTLA4-Ig or 2 µg/ml of an anti-EGF receptor antibody (Oncogen Science, Uniondale, N.Y.) in the presence of either 2 mM $Ca^{2+}$ and $Mg^{2+}$ or 15 mM EDTA with 50 µl of protein A-Sepharose (Repligen), for 2–4 hr at 4° C. The protein A-Sepharose beads were then washed three times with lysis buffer. The immunoprecipitated proteins were analyzed by SDS-PAGE (8–10.5% gradient gel) followed by autoradiography.

Immunohistology.

Murine (Balb/c) lymphoid and nonlymphoid tissues were removed and frozen in liquid nitrogen. Six-micrometer cryostat tissue sections were prepared, mounted on glass slides, and fixed with ice-cold acetone. The fixed sections were stained using 50 µg/ml of CD6-Rg or human IgG1 (Sigma) in a solution of PBS containing 1 mM $Ca^{2+}$ and $Mg^{2+}$, 10% BSA, and 10% normal goat serum (NGS) (staining buffer) for 1 hr at room temperature. The slides were washed three times in staining buffer and incubated with a 10 µg/ml of fluorescein-conjugated, affinity-purified goat anti-human IgG antibody (Tago) for 1 hr at room temperature. After washing three times with staining buffer, the slides were examined by fluorescence microscopy.

Results

CD6 Receptor Globulin, CD6-Rg.

The CD6-Rg fusion gene was constructed by fusing a cDNA fragment encoding the 400-amino acid extracellular domain of CD6 (Aruffo et al, J. Exp. Med. 174:949 (1991)), including its amino acid terminal signal sequence, onto a cDNA fragment encoding the hinge (H), CH2, and CH3 domains of human $IgG_1$ and subcloned into the mammalian expression vector CDM7B⁻(Aruffo et al, Cell 61(7):1303 (1990)) as described above. The cDNA fragment encoding the IgG constant domain contains three point mutations. These amino acid substitutions result in the impaired binding of IgG Fc domains to FcRI, II, and III.

The CD6-Rg protein used in this study was obtained by transient expression in COS cells and purified by absorption to, and elution from, a protein A column (Aruffo et al, Cell 61(7):1303 (1990)). D6-Rg is expressed as a covlanet homodimer and is recognized by all anti-CD6 mAb tested in an ELISA assay (T12, 2H1, MBG6, and G3-6). The previously described CD5-Rg (Aruffo et al. Proc. Natl. Acad. Sci. USA 89:10242 (1992)), ELAM1-Rg (Walz et al, Science 250:1132 (1990)), and CTLA4-Ig (Linsley et al, J. Exp. Med. 174:561 (1991)) fusion proteins and/or human IgG1 were used as isotype matched controls in all the binding and immunoprecipitation studies.

CD6-Rg Binding to Human and Murine Cells.

The binding of CD6-Rg to a number of human and murine cell lines was examined by indirect immunofluorescence using flow cytometry. CD6-Rg bound to a subset of the cell lines examined (FIG. 8). Among the cell lines which showed the brightest fluorescence intensity following CD6-Rg staining were the human breast epithelial-derived cell line HBL-100, the human colon carcinoma-derived cell line H3719, the melanoma-derived cell line H3606, the EBV-transformed human B cell line LCL, and the human fibroblast cell lines GM0833 and IMR90. Among the cell lines exhibiting intermediate fluorescence intensity following CD6-Rg binding were the lymphoid cell lines Jurkat, Peer, and HUT78. A number of other lymphoid cell lines including HPBALL, JM, H9, LTR228, and Raji exhibited no binding to CD6-Rg. None of these cell lines exhibited significant binding to the control fusion protein CD5-Rg. The binding to HBL-100 cell line was further characterized.

Figure 9B:
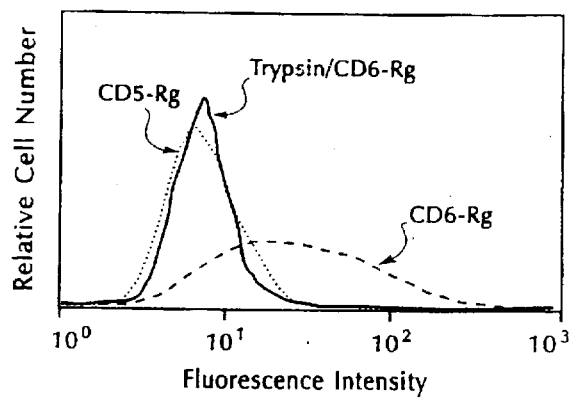

Binding of increasing concentrations of CD6-Rg to the HBL-100 cell line showed that the interaction of CD6-Rg with this cell line was dose dependent and saturable (100 µg/ml, FIG. 9 A). Treating these cells with trypsin abolished CD6-Rg binding (FIG. 9B), while neuraminidase or N-glycanase treatment only slightly decreased CD6-Rg binding. The binding of CD6-Rg to HBL-100 was in part EDTA sensitive when the chelator was added before the CD6-Rg/HBL-100 binding, but not after (FIG. 10). In addition CD6-Rg bound very weakly to this cell line in PBS; however, addition of either $Ca^{2+}$ or $Mg^{2+}$ (2 mM final concentration) resulted in strong CD6-Rg binding to HBL-100 cells.

The ability of the anti-CD6 mAb MGB6 and G3-6 to block the binding of CD6-Rg to HBL-100 cells was examined. The MGB6 mAb was able to block CD6-Rg binding to HBL-100 in a concentration-dependent manner (FIG. 11), while the G3-6 mAb was unable to block CD6-Rg binding to HBL-100 cells at concentrations as high as 0.02 mg/ml (FIG. 11).

Effects of Cytokines on CD6-Rg Binding.

Cytokines regulate the expression of a number of cell surface proteins. The effect of cytokines on the expression of the CD6-binding protein(s) expressed by HBL-100 cells was examined. Treatment of the cells with a mixture of IL-Iβ, TNFα, and IFN-γ resulted in the downregulation of CD6 ligand(s) expression (FIG. 12). Treatment with each of the cytokines alone or with pairwise combinations of the cytokines showed that a mixture of TNFα and IFN-γ was predominantly responsible for the downregulation of CD6 ligand(s) expression by these cells.

Immunoprecipitation of a CD6 Ligand.

The CD6-Rg fusion protein was used to immunoprecipitate the CD6 ligand(s) expressed by HBL-100 cells. Multiple attempts to immunoprecipitate the CD6 ligand(s) following $^{125}I$ cell surface labeling or [$^{35}$S]methionine/cysteine metabolic labeling from both cell lines were unsuccessful. In contrast, [$^{3}$H]glucosamine labeled surface glycoproteins of ~90 and ~40 kDa were obtained from HBL-100 cell lysates prior to adding CD6-Rg (FIG. 13). It is unclear if the ~40-kDa species is a unique protein or a degradation product of the ~90-kDa protein. Similarly, CD6-Rg was able to immunoprecipitate proteins of ~90 and ~40 kDa from [$^{3}$H]glucosamine-labeled H3606, a melanoma-derived cell line. CD6-Rg was unable to immunoprecipitate these proteins if EDTA was present in the cell lysate.

In addition, CD6-Rg but not CTLA4-Ig immunoprecipitated a polypeptide with a molecular mass of ~100 kDa from radiolabeled HBL-100 cell lysates in both the presence and the absence of EDTA (FIG. 13). This observation is consistent with cell binding studies which showed that CD6-Rg binding to HBL-100 cells was not completely blocked by EDTA (FIG. 10) but was completely abolished by pretreating the HBL-100 cells with trypsin (FIG. 9B). This ~100-kDa polypeptide was also immunoprecipitated from the H3606 lysates by the CD6-Rg fusion protein.

ICD6-Rg Immunohistochemistry.

Figure 14A:
Figure 14B:
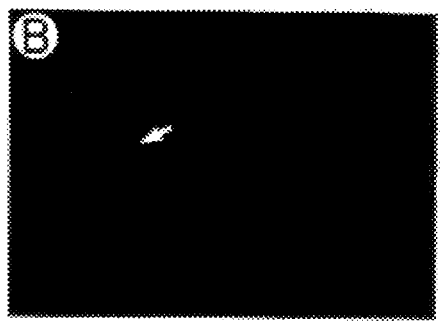
Figure 14C:
Figure 14D:
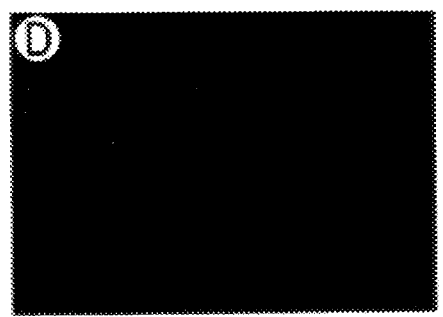
Figure 14E:
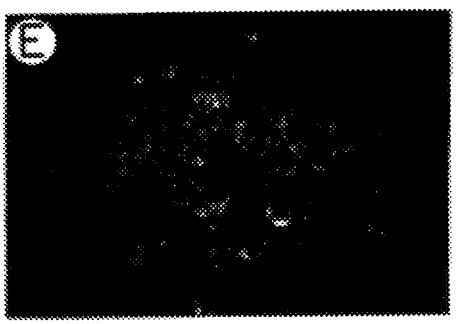
Figure 14F:

To identify tissues which expressed high levels of CD6 ligand(s) a panel of tissue sections obtained from murine brain, skin, liver, kidney, heart, spleen, lymph node, thymus, and small intestine were examined for CD6-Rg binding. Reactivity was observed in the skin, lymph node, and thymus tissue sections (FIG. 14). In the skin bright punctate staining of the dermis as well as staining of hair follicles was observed (FIG. 14A); however, human IgG$_1$ also reacted with the hair follicle, suggesting that this interaction was not mediated by the CD6 portion of the molecule. In the thymus the predominant reactivity was observed in the cortex (FIG. 14C) while in the lymph node bright staining was seen along the intermediate sinus (FIG. 14E).

Based on these observations, the binding of CD6-Rg to the murine thymic epithelial-derived cell line Z210 and to cultured human epidermal keratinocytes (EK) was examined. It was found that CD6-Rg bound to both Z210 and EK cells (FIG. 15). Binding to Z210 cells was trypsin sensitive, divalent cation-dependent, and modulated by cytokines in a similar manner to that observed with HBL-100 cells. The control fusion protein CD5-Rg did not bind to Z210 or EK cells (FIG. 15).

EXAMPLE III

Experimental Details

Cells and Culture Conditions.

TE cells and thymic fibroblasts (TF) were cultured by an explant technique as described (Singer et al, Human Immunol. 13:161 (1985); Singer et al, J. Invest. Dermatol. 92:166, (1989)). Human thymus tissue was obtained from the Department of Pathology, Duke University Medical Center, as discarded tissue from children undergoing corrective cardiovascular surgery, and thymocytes prepared as described (Denninget al, J. Immunol. 139:2573 (1989)). COS-M6 cells (ATCC, Rockville, MD) and HBL-100 cells (ATCC) were grown in DMEM containing 10% FCS, 1 mM sodium pyruvate, 0.025 µg/ml amphotericin B, 100 u/ml penicillin and 100 µg/ml streptomycin.

Monoclonal Antibodies.

Antibodies used in this study were: P3×63/Ag8 (control mAb; ATCC), 35.1 (anti-CD2; from J. Hansen, Seattle, Wash.), T12 (anti-CD6; from E. Reinherz, Boston, Mass.), NaI/34 (anti-CD1a; from A. McMichael, Oxford, England), A3D8 (anti-CD44; (Telen et al, J. Clin. Invest. 71:1878 (1983)), J4-81 and J3-119 (Pesando et al, J. Immunol. 137:3689 (1986)), phycoerythrin conjugated anti-CD4 (CD4-PE; Dako, Carpinteria, Calif.) cychrome conjugated anti-CD8 (CD8-Cy; Pharmingen, San Diego, Calif.), and the blind panel of 479 mAbs from the 5th International Workshop on Human Leukocyte Differentiation Antigens (Shaw, Concepts of cross-lineage (blind panel) analysis of expression of differentiation antigens. In: Leukocyte Typing, Schlossman et al, eds, Oxford University Press, Oxford (1994)).

Detection of Cell Surface Antigens.

Unfixed, cultured TE cells, TF, COS cells or HBL-100 cells were suspended in either PBS, TBS (0.9M NaCl, 50 mM Tris-HCl pH 7.3; with or without 5 mM CaCl$_2$, 5 mM MgCl$_2$ or 5 mM MnCl$_2$) or DMEM (with or without 10 mM EDTA) containing 2% BSA and 0.1% NAN$_3$. Cells were incubated with CD6-Rg (Wee et al, Cell. Immunol. (1994)) or with CD5-Rg (Arrufo et al, Proc. Natl. Acad. Sci. USA 89:10242 (1992)), ELAM-Rg (Walz et al, Science 250:1132 (1990)), CTLA4-Rg recombinant fusion protein (Linsley et al, J. Exp. Med. 174:561 (1991)), or human IgG (Sigma, St. Louis, Mo.) as controls (100 µg/ml) for 30 min at 4° C. and washed with PBS containing 2% BSA and 0.1% NAN$_3$. Fluorescein conjugated goat anti-human IgG$_1$ (Kirkegaard & Perry Laboratories, Inc., Gaithersburg, Md.) was used as a secondary reagent. Cells were analyzed on either a Prifile II flow cytometer (Coulter Corp., Hialeah, Fla.) or a FACStar$^{Plus}$ flow cytometer (Becton-Dickinson, Inc., Mountain View, Calif.) and data was processed using the software program PC-Lysys. To determine trypsin sensitivity of fusion protein interactions, cells were incubated with 0.2% trypsin in PBS containing 1 mM EDTA for 30 min at 37° C. and washed extensively prior to reactivity with fusion proteins. Three color immunofluorescence studies were performed.

TE-Thymocyte Rosette Binding Assay.

TE-thymocyte rosette binding assays were performed as described (Singer et al, Proc. Natl. Acad. Sci. USA 83:6588 (1986)). Thymocytes were separated into CD1$^+$(immature, CD6$^{lo}$) or CD1$^-$(mature, CD6$^{hi}$) subpopulations by indirect immunofluorescent staining with NaI/34 and goat anti-mouse IgG followed by fluorescence activated cell sorting using a FACStar$^{Plus}$ fluorescence activated cell sorter. Thymocyte subpopulations were >95% pure on reanalysis of sorted cells. Mabs used in assays of TE-thymocyte binding were used at or in excess of saturating binding titers.

COS Cell Transfection and Binding Studies.

Stable lines of CD6-expressing COS cells were constructed by co-transfection of plasmid CD6-15 containing the CD6 gene under the control of a CMV promoter (Aruffo et al, J. Exp. Med. 174:949 (1991)) and the pSVneo plasmid containing the bacterial neomycin resistance gene driven by an SV40 promoter as described (Liao et al, J. Immunol. 151:6490, (1993)). COS cells expressing CD6 were identified in indirect immunofluorescence assays using mAb T12. CD6+ and CD6− cells were cloned using a Becton-Dickinson FACStar$^{Plus}$ fluorescence activated cell sorter.

CD6-expressing COS cells (COS-CD6) and control COS cells transfected with pSVneo (COS-neo) were used in suspension binding assays with TE cells. To differentiate between COS cells and TE cells, TE cells were metabolically labelled with 1 µM calcein AM (Molecular Probes, Eugene, OR) for 15 min at 37° C. in PBS prior to harvest. Calcein AM-labelled cells are fluorescent and can be differentiated from non-labelled cells by fluorescence microscopy.

Screening of MAbs for Inhibition of CD6-Rg Binding to TE Cells.

Mabs from the blind panel of the 5th International Workshop on Human Leukocyte Differentiation Antigens and a panel of anti-integrin mabs were screened for reactivity to the surface of TE cells. Of the 154 mAbs that reacted with TE cells, 126 were used in this assay. TE cells (10$^5$) were incubated with ascites or purified mAb at a dilution of 1:100 for 15 min at 4° C. Either CD5-Rg (5µg) or CD6-Rg (5µg) were added to this mixture and allowed to react for 2 hrs at 4° C. After washing with PBS containing 2% BSA, CD5-Rg and CD6-Rg were labelled with a fluorescein-conjugated antiserum specific for the Fc portion of human IgG (Sigma). To account for any cross-reactivity with murine Ig that may have occurred with fluorescein-conjugated anti-human IgG, binding was determined as the difference in fluorescence (ΔFL) between samples containing CD6-Rg and CD5-Rg. The ΔFL of samples pre-incubated with control mAb P3 represented 100% binding.

Antibody Blocking Studies.

MAb J4-81 was purified from ascites using a protein G-sepharose column (Pierce, Rockford, Ill.) and biotinylated with sulfo-NHS-biotin (Pierce) as recommended by the manufacturer. Biotin-j4-81 (1 µg/ml) was bound to the surface of TE cells in the presence of variable doses of mAbs A3D8, J4-81 or J3-119. After incubation with FITC-conjugated streptavidin (Southern Biotechnology Associates, Inc., Birmingham, Ala.), cells were washed, fixed with 0.4% paraformaldehyde and analyzed by flow cytometry.

Immunoprecipitation and Protein Labelling Conditions.

TE cells were metabolically labelled with 120 μCi/ml $^3$H-glucosamine (New England Nuclear, Boston, Mass.), harvested and immunoprecipitated as previously described (Wee et al, Cell. Immunol. (1994)). TE cell surface proteins were labelled with $^{125}$I (New England Nuclear) using lactoperoxidase as previously described (Jones, Analysis of radiolabeled lymphocyte proteins by one- and two-dimensional polyacrylamide gel electrophoresis. In: Selected methods in cellular immunology. Mishell and Shiigi, eds. W. H. Freeman and Company, New York, pp. 398–440 (1980)).

Protein Cross-Linking.

TE cells, surface labelled with $^{125}$I, were incubated with mAbs (1:100 ascites), purified immunoglobulin (200 μg/ml) or recombinant immunoglobulin fusion proteins (200 μg/ml) for 2–4 hours in DME/5% FBS. After extensive washing with cold PBS, bound immunoglobulins were cross-linked to cell surface proteins with 1 mM DTSSP (Pierce) in PBS for 60 min at 4° C. DTSSP was inactivated with 20 mM Tris-HCl (pH 8.0) and the cells were washed with cold PBS. Cells were lysed in PBS containing 1% NP-40, 1 mM PMSF, 0.1 mM TLCK and 0.1% NAN3. Immunoglobulin complexes were purified with protein A-sepharose beads (Sigma). Prior to SDS-PAGE, protein complexes were solubilized with SDS loading buffer (2% SD, 10 mM Tris-HCl pH 7.4, 20% glycerol, bromphenol blue) containing 2% 2-mercaptoethanol (2-ME) to cleave the cross-linker. To confirm identity of proteins, purified protein complexes were treated with 0.2% trypsin in 1 mM EDTA for 30 min at 25° C. (Patel et al, Virology 149:174 (1986)) prior to solubilization and cross-linker cleavage. After electrophoresis of proteins in discontinuous SDS-polyacrylamide gels, the gels were fixed in 40% methanol, impregnated with Amplify$^R$ reagent (Amersham, Arlington Heights, Ill.) dried and exposed to autoradiography film or imaged using a PhorphorImager System (Molecular Dynamics, Sunnyvale, Calif.).

Immunohistology.

Normal human tissues were obtained as discarded tissue from the Department of Pathology, Duke University Medical Center and frozen in liquid nitrogen. Indirect IF assays of mAb reactivity on acetone fixed tissue sections were performed as described (Haynes et al, J. Invest. Dermatol. 768:323 (1982)).

Results

Effect of Anti-CD6 Antibodies and CD6-Rg on TE-Thymocyte Binding.

The role of CD6 in the binding of thymocytes to TE cells was determined using a TE-thymocyte suspension binding assay. Both antibody to CD6 (T12) and recombinant CD6-immunoglobulin fusion protein (CD6-Rg) inhibited the binding of thymocytes to TE cells (FIG. 16). As previously reported (Patel and Haynes, Semin. Immunol. 5:283 (1993)), anti-CD2 mAb 35.1 (as a positive control) inhibited TE-thymocyte binding by 76±5% (p<0.003). Anti-CD6 antibody T12 inhibited TE-thymocyte binding by 49±9% (p<0.015). Similarly, the CD6 human Ig fusion protein, CD6-Rg, inhibited TE-thymocyte binding by 35±9% (p<0.05). Addition of a combination of saturating amounts of mAbs 35.1 and T12 to TE-thymocyte binding assays resulted in a level of inhibition of binding (74±10% inhibition) that was not significantly different from blocking by mAb 35.1 alone. Nonetheless, the data with anti-CD6 mAb and CD6-Rg suggested that CD6 may be an adhesion molecule that participates in the binding of thymocytes to TE cells, and that there may be a ligand for CD6 on human TE cells.

Binding Of CD6-Expressing COS Cells to TE Cells.

Although inhibition of TE-thymocyte binding with both anti-CD6 antibody and CD6-Rg was suggestive that CD6 was an adhesion molecule, inhibition of TE-thymocyte binding may have occurred because of stearic hinderance. To confirm that CD6 was an adhesion molecule, stable transfectants of CD6-expressing COS cells (COS-CD6) were constructed (FIG. 17). COS cells transfected with pSVneo only (COS-neo) did not bind well to TE cells (6±1% COS-neo binding TE cells), whereas COS-CD6 did bind to TE cells (25±2% COS-CD6 binding TE cells, p<0.01) (FIG. 17). The specificity of the COS-CD6/TE binding was examined by testing for the inhibition of COS-CD6/TE binding by CD6 mAb T12. Compared to control mAb P3 and COS-neo cells (6±1% COS-neo binding TE), CD6 mAb T12 completely inhibited the binding of COS-CD6 to TE cells (5±1% COS-CD6 binding TE, p<0.01) to baseline levels of binding (FIG. 17), confirming that COS-CD6/TE binding was CD6-specific.

Effect of Anti-CD6mAb on the Binding of Thymocyte Subsets to TE Cells.

The role of CD6 in the binding of subsets of thymocytes was determined by examining the expression of CD6 on thymocyte subsets, and by testing the binding of sorted mature versus immature thymocyte subsets to TE cells in the presence of CD6 mAbs. Expression of CD6 on thymocyte subsets was determined by three color immunofluorescence and flow cymetry (FIG. 18). While all thymocytes expressed CD6, immature CD4+CD8+ double positive (DP) thymocytes were CD6$^{lo}$ and the mature CD4+CD8− or CD4−CD8+ single positive (SP) thymocytes were CD6$^{hi}$.

To determine the role of CD6 in the binding of thymocyte subsets to TE cells, thymocytes were separated into CD1+ and CD1− subsets by fluorescence activated cell sorting. CD1 was chosen because CD1+ thyocytes are the DP CD6$^{lo}$ cells and CD1− thymocytes are the SP CD6$^{hi}$ cells, and CD1 mAbs do not inhibit TE-thymocyte binding (Patel and Haynes, Semin. Immunol. 5:283 (1993)). Both CD1+ and CD1− thymocytes bound well to TE cells (45±4% and 54±6%, respectively, p=NS). CD2 mAb 35.1 inhibited the binding of immature thymocytes (77±9% inhibition) to a greater degree than that of mature thymocytes (52±11% inhibition) (p<0.01). CD6 mAb T12 also inhibited the binding of both immature (22±7% inhibition) and mature (39±17% inhibition) thymocytes to TE cells (p<0.25) (FIG. 19).

CD6-Rg Binding to Cells of the Thymic Microenvironment.

Figure 20A:
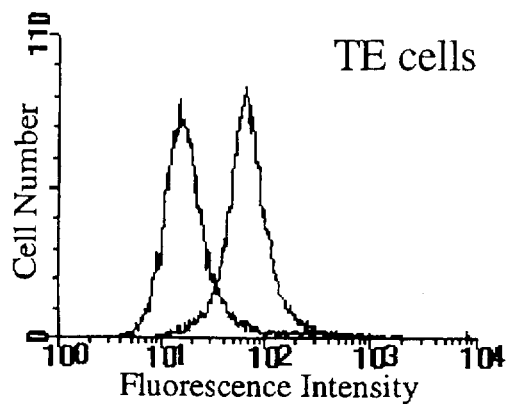
Figure 20B:
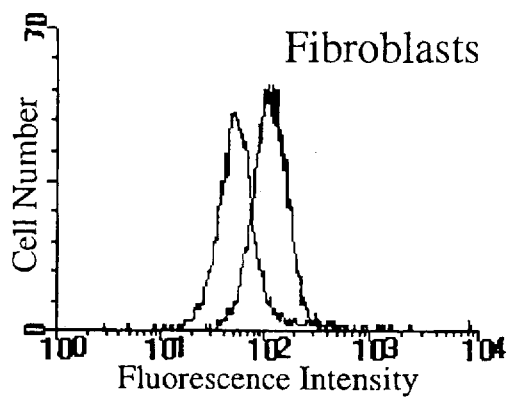
Figure 20C:
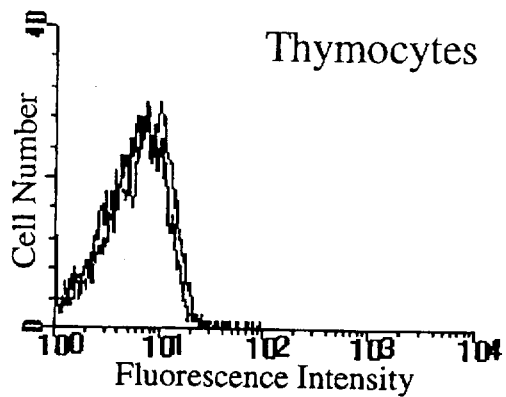
Figure 20D:
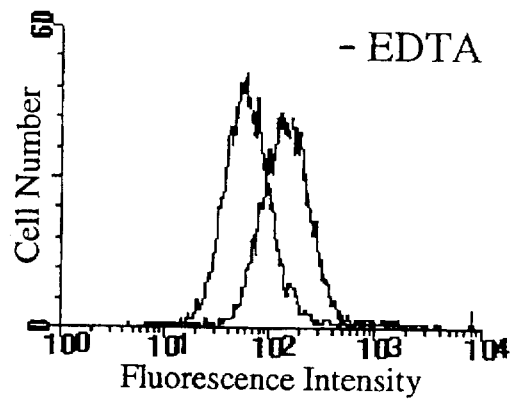
Figure 20E:
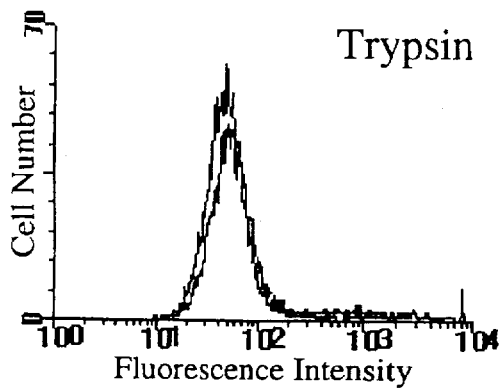
Figure 20F:
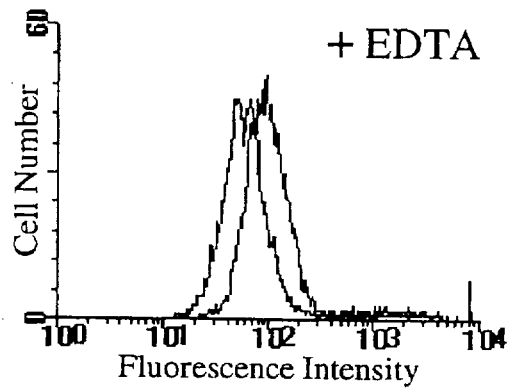
Figures 21A, 21B:
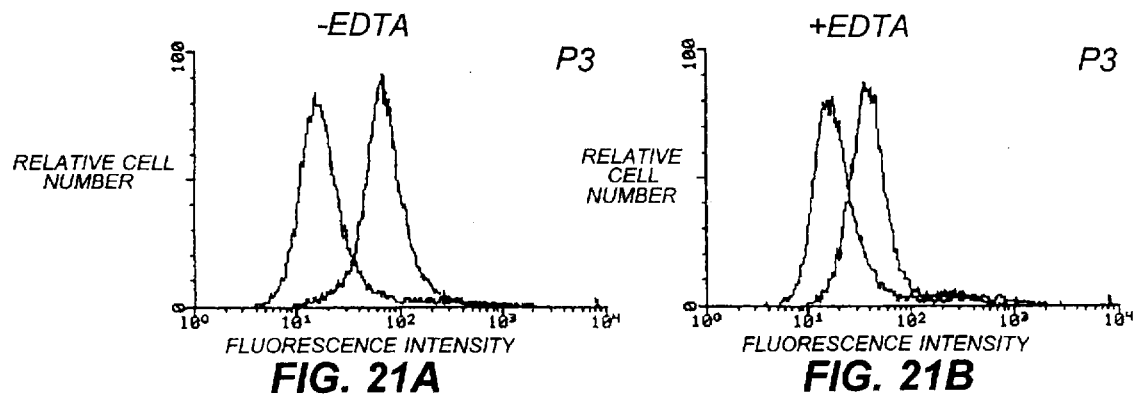
Figures 21C, 21D:
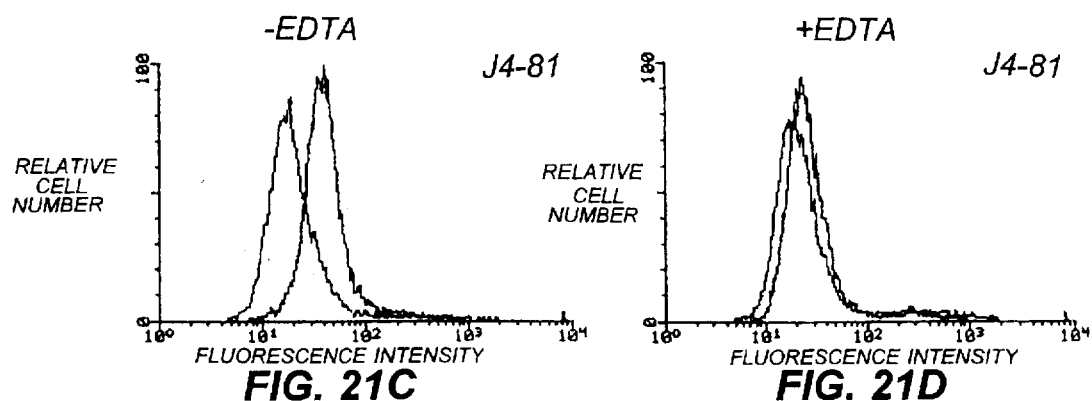
Figures 21E, 21F:
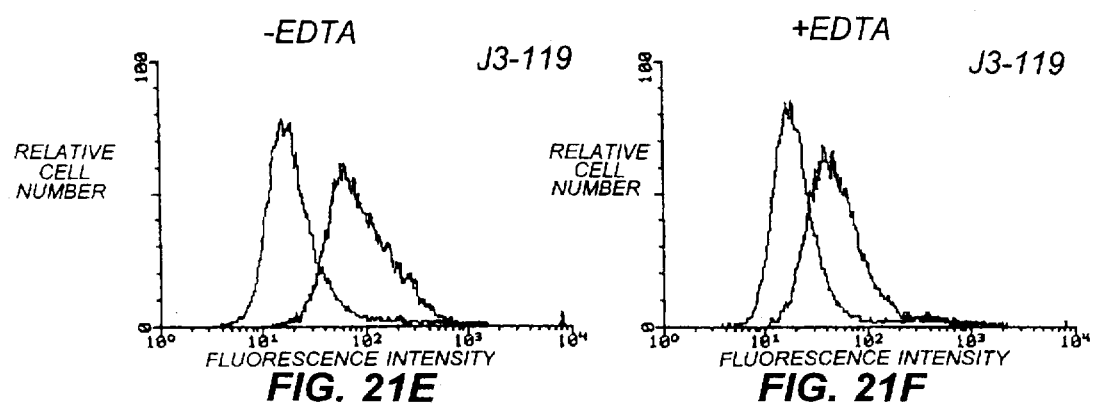
Figure 21G:
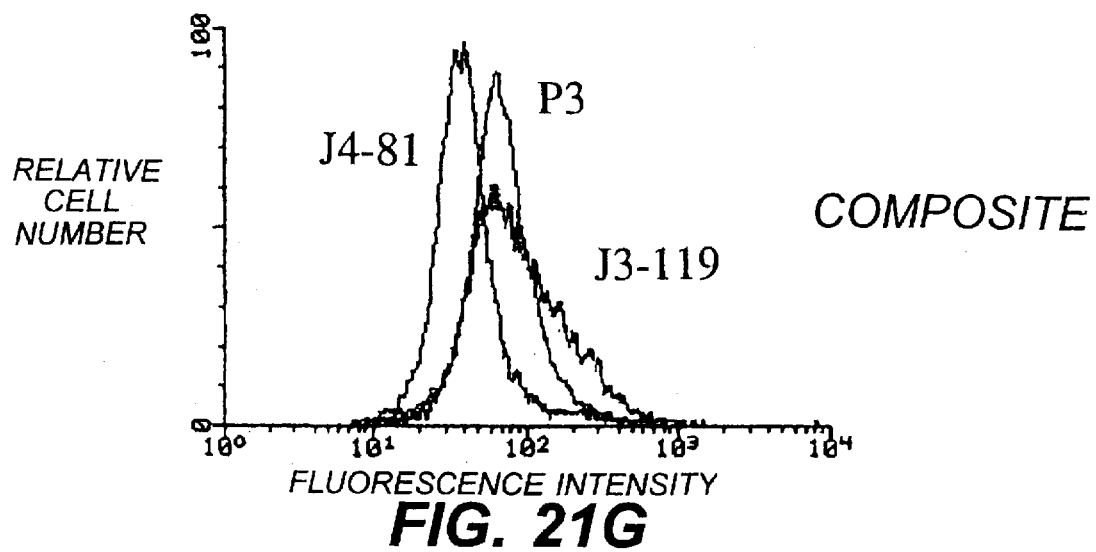
Figure 21H:
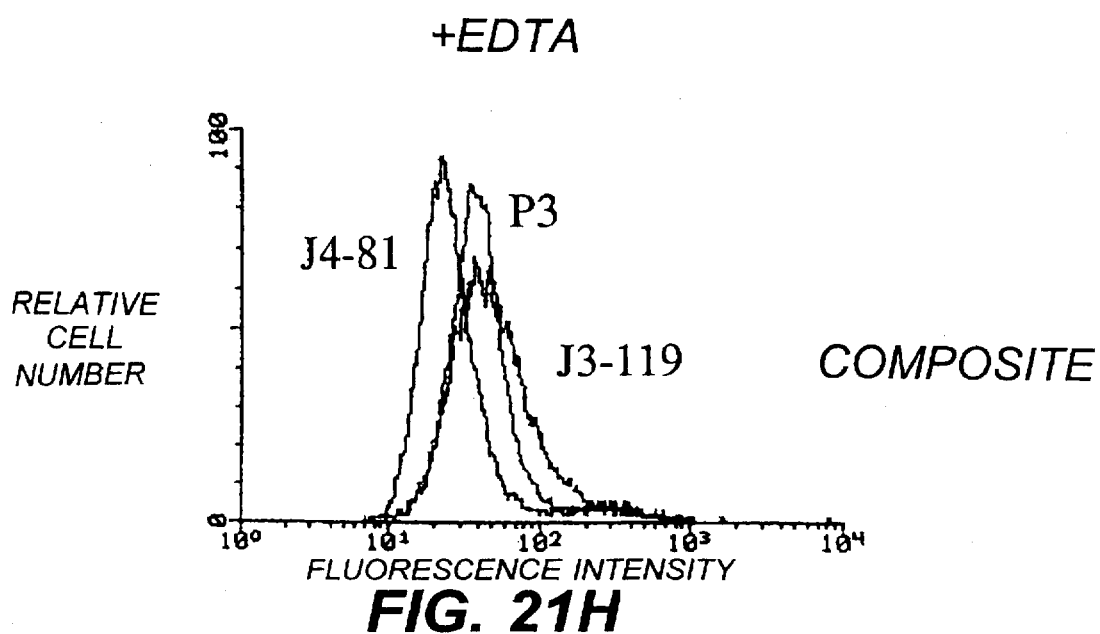

The ability of CD6-Rg fusion protein to bind to TE cells, thymic fibroblasts and to thymocytes was determined by indirect IF and flow cytometry. CD6-Rg bound to the surface of TE cells as well as to thymic fibroblasts, but not to thymocytes (FIG. 20A). Binding of CD6-Rg to TE cells was trypsin-sensitive and partially dependent upon divalent cations (FIG. 20B). CD6-Rg bound well to TE cells in a buffer containing DME and 5% FBS, but in the presence of 10 mM EDTA, binding of CD6-Rg to TE cells was inhibited by 54±4% (N=5, p<0.001, FIG. 20B). To further evaluate the divalent cation-dependence of CD6-Rg binding, CD6-Rg binding was determined in buffers containing 5 mM CaCl$_2$, 5 mM MgCl$_2$ or 5 mM MnCl$_2$. While both CaCl$_2$ and MnCl$_2$ enhanced the binding of CD6-Rg to TE cells (144±5%, p=0.01, and 318±22%, P<0.01, respectively), MgCl$_2$ did not affect CD6-Rg binding (94±2%, p=NS).

Antibody-Mediated Inhibition of CD6-Rg Binding to TE Cells.

To begin to identify the CD6 ligand(s), a panel of 479 mAbs from the 5th International Workshop on Human Leukocyte Differentiation Antigens was screened for reactivity to the surface of TE cells by indirect immunofluorescence and flow cytometry (Shaw, Concepts of cross-lineage (blind panel) analysis of expression of differentiation antigens. In: Leukocyte Typing, Schlossman et al, eds, Oxford University Press, Oxford (1994)). Of the 154 mAbs that reacted with the surface of TE cells, 126 mAbs were used in assays to inhibit the binding of CD6-Rg to TE cells. Of the 122 mAbs that did not react with the secondary antiserum, only one (J4-81) inhibited the binding of CD6-Rg to TE cells. MAb J4-81 inhibited the binding of CD6-Rg to TE cells by 60±7% (N=10, p<0.001) and to the breast cell line HBL-100 by 40±3% (N=3, p<0.02) (Table 4), which has also been shown to bind CD6-Rg (Wee et al, Cell. Immunol. (1994)). In flow cytometry assays, both TE cells and HBL-100 cells reacted strongly with mAb J4-81.

TABLE 4

MAb inhibition of CD6-Rg binding to TE and HBL-100 cells.

| Cell Type | mAb | Δ Fluorescence* | % Binding‡ | % Inhibition§ |
|---|---|---|---|---|
| TE cells | P3 | 52 | 100 | 0 |
| | CD9 | 60 | 115 | -15 |
| | CD24 | 48 | 92 | 8 |
| | CD40 | 48 | 92 | 8 |
| | CD46 | 57 | 110 | -10 |
| | CD51 | 46 | 88 | 12 |
| | CD54 | 44 | 85 | 15 |
| | CD58 | 45 | 87 | 13 |
| | CD59 | 52 | 100 | 0 |
| | CD63 | 53 | 102 | -2 |
| | CD66 | 56 | 108 | -8 |
| | J4-81 | 21 | 40 | 60 |
| HBL-100 | P3 | 58 | 100 | 0 |
| | J4-81 | 34 | 59 | 41 |

*ΔFluorescence = Fluorescence (CD6-Rg) - Fluorescence (CD5-Rg). Shown is the binding of CD6-Rg compared to control (CD5-Rg) in the presence of selected mAbs that bind well to the surface of TE cells.
‡% Binding = 100 [ΔFL (experimental mAb) - ΔFL(P3)]/ΔFL(P3).
§% Inhibition = 100 [ΔFL(P3) - ΔFL (experimental mAb)]/ΔFL(P3).

MAb J3-119, reported to react with a second epitope on the molecule detected by J4-81 (Pesandro et al, J. Immunol. 137:3689 (1986)), enhanced the binding of CD6-Rg to TE cells (FIG. 21) by 48±5% (N=6, P<0.005), and to HBL-100 cells by 45±11% (N=3, p<0.1). To confirm that mAb J3-119 recognized the same protein as mAb J4-81, the ability of mAb J3-119 to block the binding of biotinylated J4-81 to TE cells was tested. While mAb A3D8 to CD44 (which binds well to the surface of TE cells had no effect on J4-81 binding, both J4-81 and J3-119 mAbs inhibited the binding of biotinylated J4-81 (99% and 82%, respectively) (FIG. 22). Moreover, mAb J4-81 modulated surface expression on B cells of the antigen detected by J3-119 (Pesandro et al, J. Immunol. 137:3689 (1986)).

To further establish that mAb J4-81 recognized a ligand for CD6, the ability of J4-81 to inhibit the CD6-specific binding of COS-CD6 cells to TE cells was tested. MAb J4-81 significantly inhibited the binding of TE cells to COS-CD6 cells (87±1%, N=3, p<0.001), thus confirming that J4-81 recognized a CD6 ligand.

MAb J4-81 and CD6-Rg Bind 100 kDa TE Cell Proteins that are Identical.

To identify the TE cell surface protein(s) that bound to CD6-Rg, a strategy was devised whereby CD6-Rg interactions with CD6 ligand(s) on surface $^{125}$I labelled TE cells were stabilized with DTSSP, a clearable homobifunctional cross-linking reagent reactive with free amino groups, and CD6-Rg containing complexes were purified using protein A-sepharose beads. Using this strategy, CD6-Rg specifically reacted with a 100 kDa TE cell surface protein (FIG. 23). MAb J40-81 cross-linked to $^{125}$I labelled TE cells also yielded an 100 kDa protein that migrated with the 100 kDa protein recognized by CD6-Rg (FIG. 23). Trypsin digestion studies showed that the 100 kDa protein identified by J4-81 had an identical trypsin digestion pattern to the 100 kDa protein identified by CD6-Rg (FIG. 23), indicating that both proteins were identical. MAb J4-81 also specifically immunoprecipitated an 100 kDa protein from extracts of TE cells metabolically labelled with $^3$H-glucosamine.

The 100 kDa CD6 Ligand is a Divalent Cation-Independent Ligand for CD6.

The immunoprecipitation studies (above) showed that CD6-Rg was able to immunoprecipitate a 100 kDa protein in the presence and absence of divalent cations. Thus, the 100 kDa protein may be a divalent cation-independent CD6 ligand. Further, J4-81 only partially inhibited the binding of CD6-Rg to TE cells in the presence of divalent cations, suggesting that there may be more than one ligand for CD6. MAb J4-81 nearly completely inhibited (80±10% inhibition, p<0.1) CD6-Rg binding to TE cells in the presence of EDTA (FIG. 21), confirming that it is primarily involved in divalent cation-independent CD6-CD6 ligand interactions. In contrast, mAb J3-119 enhanced CD6-Rg binding by 47±7% (p<0.1) in the absence of divalent cations (FIG. 21).

Tissue distribution of mAb J4-81 reactivity. The tissue distribution of the 100 kDa glycoprotein recognized by J4-81 was examined on frozen sections of a variety of human tissues by indirect IF (Table 5). The reactivity of mAb J4-81 with human tissues and cell lines was broad. While CD6 was expressed on thymocytes in postnatal human thymus, the 100 kDa CD6 ligand was expressed on cortical and medullary TE cells and Hassall's bodies (FIG. 24). In tissues other than thymus, J4-81 reacted with epidermal keratinocytes, gut epithelium, breast epithelium, pancreatic acinar and islet cells, hepatocytes, renal tubular epithelium, neurons of the cerebral cortex, and fibroblasts.

TABLE 5

Reactivity of mAb J4-81 in sections of normal human tissues.

| Tissue (Number Tested) | J4-81 Reactivity |
|---|---|
| Thymus (5) | Hassall's bodies, epithelium, fibroblasts |
| Spleen (2) | Scattered mononuclear cells |
| Lymph Node (1) | Scattered mononuclear cells |
| Tonsil (2) | Pharyngeal epithelium, lymphocytes |
| Appendix (1) | Fibroblasts, lymphoid cells, epithelium |
| Colon (2) | Fibroblasts, epithelium |
| Esophagus (2) | Basal epithelium |
| Breast (2) | Epithelium, fibroblasts |
| Liver (2) | Hepatocytes, Kupfer cells, fibroblasts |
| Pancreas (2) | Acinar and islet cells |
| Kidney (2) | Fibroblasts, subset of tubules, Bowman's capsule |
| Skin (2) | Perivascular fibroblasts, epithelium |
| Brain (2) | Neurons |

The cell types reacting with mAb J4-81 in each of the tissue types are listed.

All documents cited above are hereby incorporated in their entirety by reference.

One skilled in the art will appreciate from a reading of this disclosure that various changes in form and detail can be made without departing from the true scope of the invention.

What is claimed is:

1. An isolated and purified mammalian CD6 ligand having a molecular weight of about 35 kDa as determined by sodium dodecyl sulfate polyacrylamide gel electrophoresis under reducing conditions, wherein the binding of said ligand to 0 CD6 is divalent cation independent.

2. An isolated and purified mammalian CD6 ligand having a molecular weight of about 105 kDa as determined by sodium dodecyl sulfate polyacrylamide gel electrophoresis under reducing conditions, wherein the binding of said ligand to CD6 is divalent cation independent.

3. An isolated and purified mammalian CD6 ligand having a molecular weight of 90 kDa as determined by sodium dodecyl sulfate polyacrylamide gel electrophoresis under reducing conditions, wherein the binding of said ligand to CD6 is divalent cation dependent.

4. The ligand according to claim 3 wherein said ligand is isolated and purified from a thymic epithelial cell.

5. The ligand according to claim 4 wherein said thymic epithelial cell is a human cell.

6. A composition comprising the CD6 ligand according to one of claims 3, and a pharmaceutically acceptable carrier.

* * * * *